(12) United States Patent
Mide et al.

(10) Patent No.: US 10,661,028 B2
(45) Date of Patent: May 26, 2020

(54) FLUID TRANSFER DEVICES

(71) Applicant: CONCEPTOMED AS, Ballstad (NO)

(72) Inventors: Christian Mide, Ballstad (NO); Marius Andresen, Oslo (NO); Rolf Blomvågnes, Rong (NO); Kevin Geers, Oslo (NO)

(73) Assignee: Conceptomed AS, Ballstad (NO)

( * ) Notice: Subject to any disclaimer, the term of this patent is extended or adjusted under 35 U.S.C. 154(b) by 844 days.

(21) Appl. No.: 14/692,798

(22) Filed: Apr. 22, 2015

(65) Prior Publication Data

US 2016/0296714 A1    Oct. 13, 2016

(30) Foreign Application Priority Data

Apr. 9, 2015 (GB) .................................. 1506050.2

(51) Int. Cl.
*A61M 5/34* (2006.01)
*A61M 5/31* (2006.01)
(Continued)

(52) U.S. Cl.
CPC .......... *A61M 5/346* (2013.01); *A61M 5/3134* (2013.01); *A61M 5/3205* (2013.01);
(Continued)

(58) Field of Classification Search
CPC ...... A61M 5/346; A61M 5/347; A61M 5/348; A61M 5/3134; A61M 5/3205;
(Continued)

(56) References Cited

U.S. PATENT DOCUMENTS

| 2,047,512 A | 7/1936 | Kauffman |
| 2,875,760 A | 3/1959 | Christian |
(Continued)

FOREIGN PATENT DOCUMENTS

| DE | 883053 C | 7/1953 |
| DE | 29707813 U1 | 7/1997 |
(Continued)

OTHER PUBLICATIONS

International Search Report and Written Opinion for PCT/EP2016/057943, dated Aug. 12, 2016 (13 pages).

*Primary Examiner* — Nathan R Price
*Assistant Examiner* — Justin L Zamory
(74) *Attorney, Agent, or Firm* — Eversheds Sutherland (US) LLP

(57) ABSTRACT

A fluid transfer device may include a body member and a fluid transfer tip, wherein the fluid transfer tip may include a tapered friction fitting for a corresponding hub. The fluid transfer device also may include a disconnecting member having a front portion and a rear portion and engagement features operating between the disconnecting member and the body member. The engagement features engage with one another to inhibit the front portion of the disconnecting member from moving relative to the fluid transfer tip. The fluid transfer device is arranged such that upon application of a force to the rear portion of the disconnecting member, the disconnecting member deforms so that the engagement features are no longer in engagement with one another. This allows the front portion of the disconnecting member to move relative to the fluid transfer tip and subsequently release the hub from the friction fitting.

40 Claims, 11 Drawing Sheets

(51) Int. Cl.
*A61M 5/32* (2006.01)
*A61M 39/12* (2006.01)

(52) U.S. Cl.
CPC .............. *A61M 5/34* (2013.01); *A61M 5/344* (2013.01); *A61M 5/345* (2013.01); *A61M 5/347* (2013.01); *A61M 39/12* (2013.01); *A61M 2005/3142* (2013.01); *A61M 2005/3206* (2013.01)

(58) Field of Classification Search
CPC .................. A61M 5/344; A61M 5/345; A61M 2005/3142; A61M 2005/3206
See application file for complete search history.

(56) References Cited

U.S. PATENT DOCUMENTS

| | | |
|---|---|---|
| 4,425,119 A | 1/1984 | Berglund |
| 4,490,142 A | 12/1984 | Silvern |
| 4,820,277 A | 4/1989 | Norelli |
| 4,822,343 A | 4/1989 | Beiser |
| 4,904,244 A | 2/1990 | Harsh et al. |
| 4,907,600 A | 3/1990 | Spencer |
| 4,984,580 A | 1/1991 | Wanamaker |
| 5,201,716 A | 4/1993 | Richard |
| 5,405,330 A | 4/1995 | Zunitch et al. |
| 5,695,477 A | 12/1997 | Sfikas |
| 5,713,876 A | 2/1998 | Bogert et al. |
| 5,775,673 A | 7/1998 | Carnes, Sr. et al. |
| 5,823,997 A | 10/1998 | Thorne |
| 5,980,488 A | 11/1999 | Thorne |
| RE37,908 E | 11/2002 | Kinsey |
| D617,454 S | 6/2010 | Shaw |
| 8,012,132 B2 | 9/2011 | Lum |
| 2009/0270672 A1 | 10/2009 | Fago |

FOREIGN PATENT DOCUMENTS

| | | |
|---|---|---|
| EP | 0747087 A2 | 12/1996 |
| EP | 0787501 A2 | 8/1997 |
| EP | WO2014020090 A1 | 2/2014 |
| EP | 3027250 B1 | 3/2017 |
| FR | 2645444 A1 | 10/1990 |
| FR | 2647351 A1 | 11/1990 |
| FR | 2733916 A1 | 11/1996 |
| GB | 2209470 A | 5/1989 |
| GB | 2518741 A | 1/2015 |
| JP | H01-120852 U | 8/1989 |
| JP | H10-179737 A | 7/1998 |
| JP | 2002-028246 A | 1/2002 |
| WO | 1990/000074 A1 | 1/1990 |
| WO | 1990/000881 A1 | 2/1990 |
| WO | 1990/011789 A1 | 10/1990 |
| WO | 1996/035466 A1 | 11/1996 |
| WO | 2006/045215 A1 | 5/2006 |
| WO | 2008/086004 A1 | 7/2008 |
| WO | 2011/159136 A2 | 12/2011 |
| WO | 2013/072182 A1 | 5/2013 |
| WO | 2013/164358 A1 | 11/2013 |
| WO | 2015/014914 A1 | 2/2015 |

Figure 16
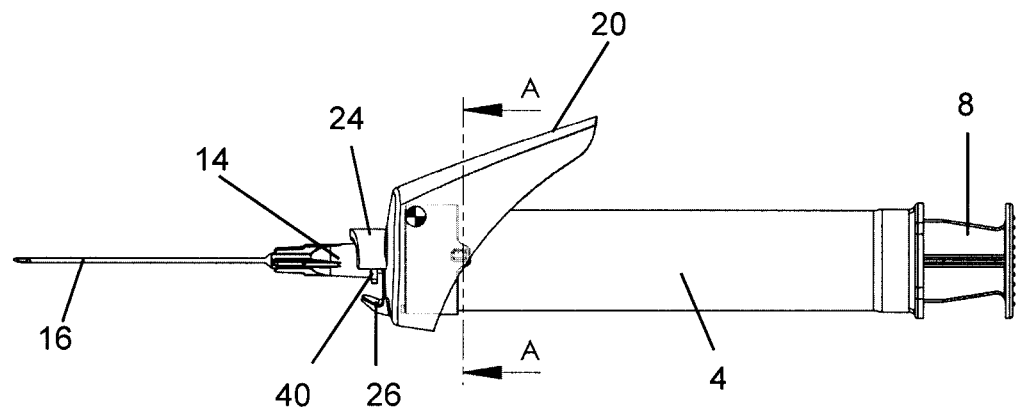
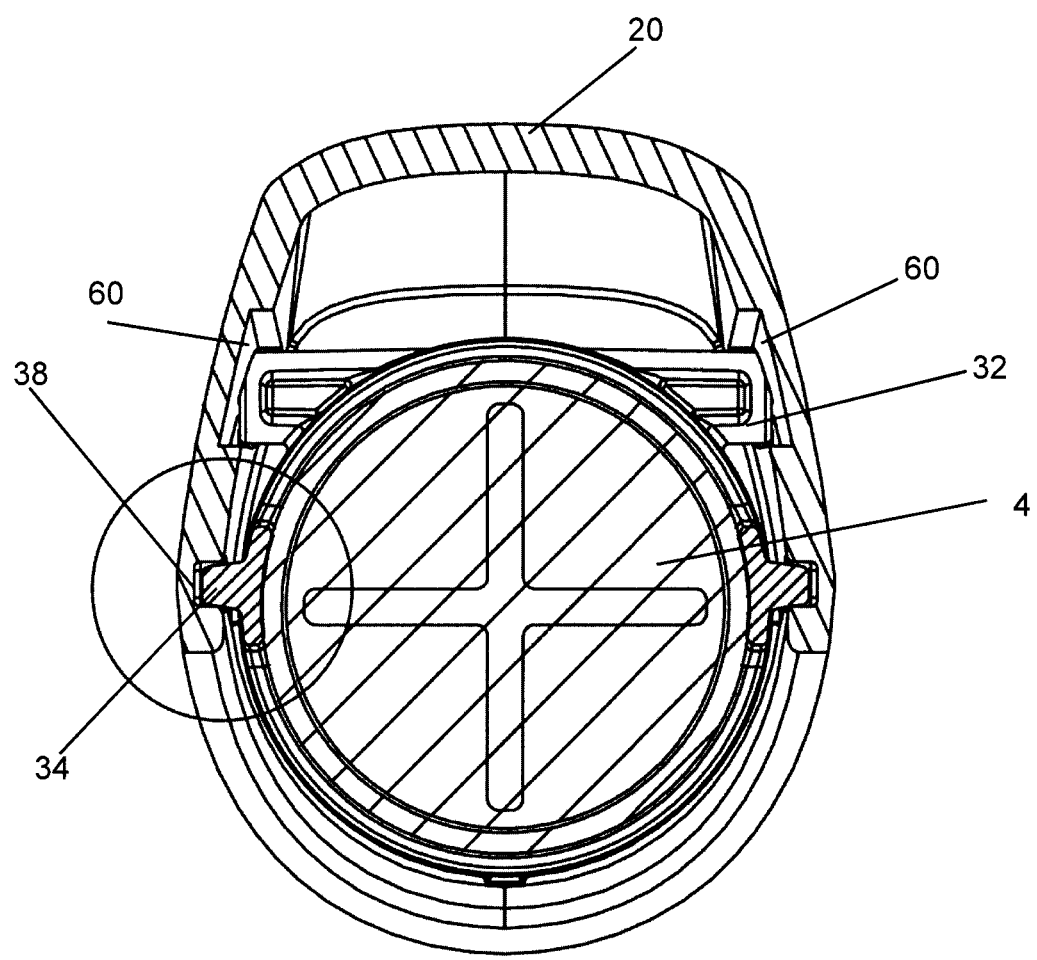
Figure 17

Figure 20
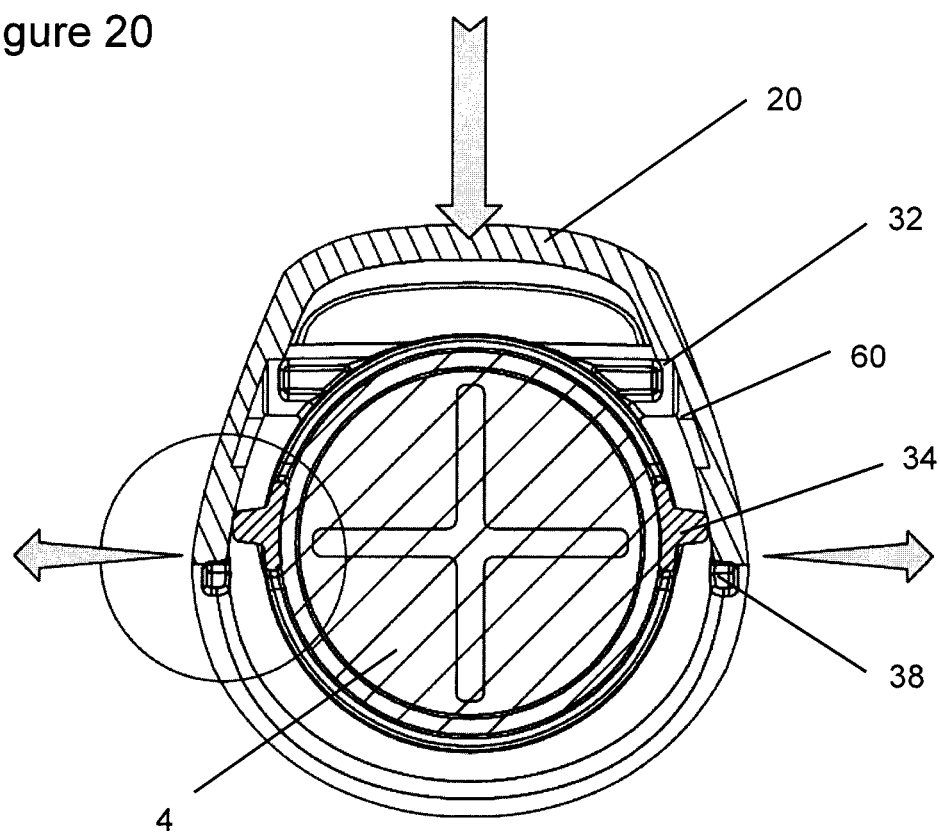
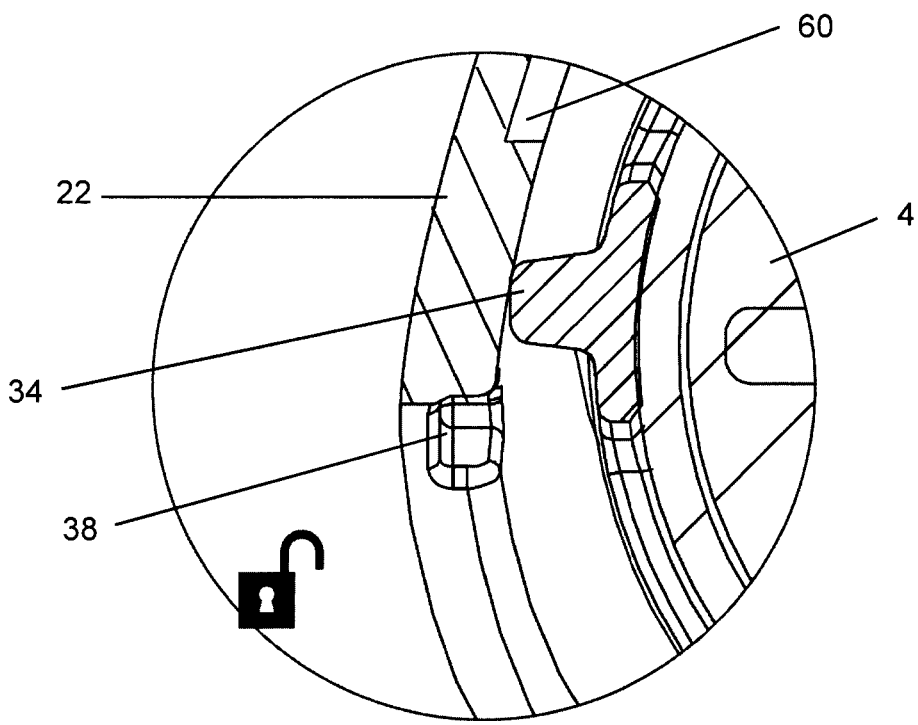
Figure 21

FLUID TRANSFER DEVICES

TECHNICAL FIELD

The present invention relates to the detachment of fluid-transferring devices and connections from a corresponding hub, and especially when transferring fluid in a medical setting. The invention may find particular use in detaching a fluid transfer device such as a syringe, or other fluid transfer connection, from a hub that is connected to a living subject to/from whom fluid is being transferred.

BACKGROUND OF THE INVENTION

In a medical setting it may be necessary or desirable to transfer fluid to/from a subject for a variety of reasons. For example, a hub connected to a needle or other cannula may be used to draw blood from a vein or to infuse fluid substances i.e., intravenous (IV) therapy. A drip is one type of IV therapy. IV therapy may be used to correct electrolyte imbalances, to deliver medications or nutrition, for blood transfusion or as fluid replacement to correct dehydration. IV therapy can also be used for chemotherapy of cancer patients. Fluid-transferring devices such as syringes may also be attached to a hub that connects a cannula for the addition or removal of fluid to/from a variety of bodily cavities, organs, or vessels. For instance, the hub may be part of an entity providing a catheter to drain urine from the bladder or kidney, to remove fluid from an abscess, to extract liquid from joints or cysts, or to administer breathing gases through a tracheal tube. A typical endotracheal tube may include a cuff inflation tube with a hub for attachment of a syringe to enable inflation to seal the trachea and bronchial tree against air leakage and aspiration of fluids. A tracheostomy tube or urinary tract catheter might also use a cuff system with a hub for connection of a syringe or other device to inject fluid to inflate a cup or balloon that holds it in place. However fluid injections using a syringe connected to a needle are one of the most common health care procedures in the world.

When transferring fluids to/from a subject, the hub with its needle, catheter or other cannula inserted in the patient is often left in-situ while the fluid-transferring device may be removed and replaced, e.g., to empty/re-fill a syringe or to change over the IV therapy. Where two medical devices that carry small fluid volumes must be connected, a standard Luer fitting is the most common means of achieving a leak-free junction. One type of Luer fitting, commonly called a "Luer lock/lok", uses an internally threaded collar surrounding a "Luer slip" friction fit (see below) tapered male tip of a syringe or the like. The projecting tip can be inserted into a corresponding female hub with an external thread, or other suitable protrusion for cooperating with the collar, and the collar screwed down on the hub to lock the connection. Such Luer lock fittings have the advantage of providing a secure connection that cannot easily come loose, but two hands are needed to hold the hub while screwing the device in/out. A more rapid form of attachment may be preferred in some circumstances, for example in an emergency situation. Another type of Luer fitting, commonly called a "Luer slip", simply uses a friction fit between a female hub and corresponding tapered male tip of a device without a threaded collar. A standard friction fit may be achieved by a 6% taper. A Luer slip attachment is common for infusing less viscous fluids, such as vaccinations, and transferring fluids where high pressures are not involved, for example when drawing blood.

A problem observed with both Luer lock and Luer slip connections is the risk of injury when detaching the fluid-transferring device from a hub on a cannula that is still connected to a patient. Although a medical practitioner might take care to hold the hub and avoid injury when unscrewing a Luer lock connection, there is a temptation with a Luer slip connection to try to pull the device from the hub e.g., with one hand. However this can easily result in the hub being tugged away from the body and causing tissue damage. Often the device may not be pulled in a straight line with the cannula connected to the hub, but rotated, and this can twist the components. The tape used to hold the hub e.g., IV port in position is often loosened from the skin and its cannula e.g., needle may even be accidentally extracted. When emptying fluid from a body cavity, for example, keeping the needle hub still when detaching the syringe can be essential to avoid diffuse cutting inside the cavity or damage of the cavity wall. In addition there is a risk of unacknowledged contamination of both the hub and the Luer tip (not only the user) when holding the very small hub with the thumb and index fingers while pulling away the male tip, the tip sliding past the user's fingers as it is released.

Moreover tugging with a single hand does not usually apply enough force even to pull the device out of a friction fitting (such as a Luer slip) and, depending on the force used when connecting the Luer slip tip to the hub, the practitioner usually needs to hold or push the hub while also pulling the device so that it becomes detached. Typically the device will be rotated simultaneously while pulling away from the hub. This jerking can result in unwanted extraction of the needle or other component connected to the hub. The connection will often be pressurised by fluid. For example, a cuff connected to a tracheostomy tube, endotracheal tube or urinary catheter often has a tight connection of the male Luer tip with two-handed operation being required to loosen the connection while the sprung piston in the female Luer hub blocks the outflow of fluid (air or liquid) from the cuff.

Several medical procedures involve targeted introduction of an empty syringe connected to a cannula or other catheter. Such procedures require careful insertion of the cannula or catheter and also careful removal of the syringe if the catheter or cannula is left in situ. The process typically involves applying negative pressure in the syringe by pulling the plunger/piston back during the inward insertion movement of the cannula or catheter towards a target inside the patient. The objective is to verify that the correct target has been reached by drawing a body liquid, e.g., blood, cerebrospinal fluid, synovial fluid from joints, bile, or urine into the syringe barrel where it can be observed. When the appropriate liquid is seen in the barrel, the user can be sure that the catheter tip is in the correct position. Some procedures involve the use of additional guiding tools, e.g., ultrasound guided cannula insertion. During such procedures the user must hold onto the ultrasound probe in addition to the syringe, and monitor the position of the cannula or catheter on a screen. After reaching the target with the tip, the operator typically needs to detach the syringe from the catheter hub. Using conventional methods this can inadvertently cause the tip to dislocate from its intended targeted original position as two handed operation is required to remove the hub. Furthermore during such ultrasound-guided techniques for catheter tip placement, the ultrasound probe is typically put aside/inactivated before the disconnection and therefore the user loses the ability to accurately monitor the position of the tip.

Ease of disconnection can be a problem not only when detaching a device from a hub connected to a patient but also when it is desired to fill/empty a device such as a syringe via a fluid hub in a quick and convenient manner. For example, when filling a syringe using a needle inserted in a vial, each time that the syringe is removed it requires two hands to firmly grasp the needle hub and the syringe to separate them while the needle remains in the vial. As mentioned above, there is again a risk of contamination as the user grasps the hub and the tip comes into contact with the fingers holding the hub.

Another situation where a user might come into contact with a needle hub is when using a blood collection tube. The blood tubes are evacuated plastic or glass containers sealed with an elastomeric septum that is pierceable by a double-ended needle to draw venous blood. Due to the piercing force and pressure differential, a secure connection to the needle assembly is required and therefore a threaded Luer lock connection is normally used rather than a Luer slip. U.S. Pat. No. 5,201,716 proposes an alternative blood specimen collection system that does not require the needle assembly to be grasped and twisted during disconnection. In this system a needle assembly is mounted with an interference fit rather than a threaded connection. A pivotally mounted lever assembly is spring-biased to hold the needle assembly in position, i.e., to provide an additional level of security over the friction fit. If the lever is actuated against its spring bias then there is only an interference fit holding the needle assembly in place. The lever can be pivoted to simultaneously release the spring bias and to apply a forward ejection force to the needle assembly.

In any situation where one hand is holding a needle hub while pulling a device away there is a risk of needlestick injury and contamination. Needle caps frequently being mislaid or forgotten can exacerbate this. This also applies when separating a needle or other contaminated component from a syringe or similar device for disposal purposes, with many needlestick injuries occurring when trying to remove sharps to throw into a bin. Usually the person handling a syringe will try to cover a contaminated needle with a cap after use, before grasping the hub to separate the needle from the syringe barrel for disposal. However, when mounting a needle cap onto the contaminated needle a person will use the large muscle groups in the arms and shoulders that work less precisely and, combined with poor depth of vision, this often results in a needlestick injury to the fingers holding the needle cap. It would be better if a needle hub could be safely released without needing to cap the needle or handle the connection.

There are various fluid transfer procedures in the medical setting that may require a very secure connection between a fluid transfer tip (e.g., provided by a syringe) and a corresponding hub. The hub may be connected to a needle or catheter inserted into an artery, vein, cavity or organ of a patient. In the field of cardiology, angiography and angioplasty procedures may inject fluids (liquid and/or air) into narrow channels at high pressure. Manual syringes and manifold sets are used for percutaneous coronary interventions and coronary diagnostic procedures such as angiography. A cardiac angiographic kit typically may include a catheter hub for connection, a catheter body of chosen size, length and stiffness, and a tip with a single end-hole to eject fluids. The catheter body is inserted into the coronary vessels, ventricles and/or peripheral vasculature. A syringe may be connected to the catheter hub to inject contrast agents or saline at pressures ranging between 250 and 800 psi, and even up to 1000 or 1200 psi (84 bar). The catheter hub has an external thread to provide a standard Luer lock connection.

Luer lock connectors have become universal, not only for joining syringes to hubs, but also for connecting small-bore medical tubing and hoses for liquids and/or gases. Luer lock connections are commonly used for vascular IV lines but also find use in other medical treatment or diagnostic systems. Tubing and hoses may use a Luer lock connection for cuff inflation systems, feeding tubes, catheters, and hoses for vascular, enteral, respiratory, neuraxial and urethral/urinary systems.

The screw connection of a Luer lock hub is often considered necessary to withstand high pressures. However a syringe, hose, or other fluid transfer device must be rotated to connect, and disconnect, its Luer lock collar to/from the hub. This can take time and requires a two-handed operation. Furthermore, when a user grips the hub to unscrew the connection there is a risk of contamination, especially where the hub may include a needle that may carry blood on its shaft. It would improve the efficiency and workflow of medical procedures if a fluid transfer device could be disconnected from a Luer lock hub more easily.

There are various devices known in the art to assist in the removal of a Luer slip hub from a fluid transfer device. Many of these devices utilise a lever member capable of pushing the hub away from the tip of the fluid transfer device. In such embodiments the positioning of the lever member on the fluid transfer device can lead to accidental release of the hub, as the lever typically requires a small amount of force to be applied to it in order to remove the hub. This accidental release could be dangerous in instances where a needle is attached to the hub as this could result in a needlestick injury.

Arrangements for removing a Luer slip hub may also be used to remove a Luer-lock hub from a fluid transfer device. Some examples of this are taught in WO2014/020090. These fluid transfer devices typically may include a threaded collar attached to a lever member. Such a lever member is capable of moving the threaded collar away from the Luer-lock hub allowing it to be released. However The Applicant has now appreciated the potential for improvement of the arrangements taught in the above-mentioned application. In particular it has been recognised that in some circumstances there might be a tendency with such devices when screwing the Luer-lock hub to the device for the lever member to pull forward and away from the fluid transfer tip. This could cause the threaded collar to move away from the fluid transfer tip and so result in a poor connection between the hub and transfer tip which could lead to the loss of fluid during use of the fluid transfer device.

SUMMARY OF THE INVENTION

The present invention seeks to address or mitigate this problem. When viewed from a first aspect the present invention provides a fluid transfer device including:
a body member;
a fluid transfer tip, the fluid transfer tip comprising a tapered friction fitting for a corresponding hub;
a disconnecting member having a front portion and a rear portion; and
engagement features operating between the disconnecting member and the body member which engage with one another to inhibit the front portion of the disconnecting member from moving relative to the fluid transfer tip;
the device being arranged such that upon application of a force to the rear portion of the disconnecting member, the disconnecting member deforms so that the engagement features are no longer in engagement with one another, thereby allowing the front portion of the disconnecting member to move relative to the fluid transfer tip and subsequently release the hub from the friction fitting.

Thus it will be seen by those skilled in the art that a fluid transfer device provides a novel mechanism for reducing the risk of accidental release of the hub from the fluid transfer tip. The engagement features ensure that the hub is only removed when a sufficient force is applied to the rear portion of the disconnecting member. The engagement features help to reduce the risk that if a user should inadvertently apply pressure to the disconnecting member, this will accidentally release the hub.

In a set of embodiments the disconnecting member is provided by a lever member. An advantage of using a lever member to disconnect the tip from a corresponding hub is that it can amplify an input force to provide a greater output force, i.e., providing leverage to push a hub away from the tip. In a set of embodiments the lever member is pivotally mounted relative to the fluid transfer tip. The mechanical advantage of a lever member can increase the force applied so that the device can be released without necessarily holding the hub, thereby enabling single-handed operation. This carries several advantages—for example the ability to maintain sterility during procedures. In the case of catheter insertion procedures, such as those previously described, it advantageously allows a user easily to detach the hub when the tip is correctly positioned without disturbing its position. In ultrasound-guided procedures it also allows the entire procedure up to and including detachment of the hub to be conducted without looking away from the ultrasound monitor.

Advantageously the disconnecting member is designed such that any potential user can apply an appropriate force to overcome the engagement features. The disconnecting member could be formed integrally with the body member—e.g., using a living hinge. In another set of embodiments the disconnecting member is a separate part from the body member.

Any suitable form of engagement features may be used. For example complementary mutually engaging coarse surfaces could be provided on the disconnecting member and body member. In a set of embodiments however the engagement features may include at least one protrusion and at least one complementary recess. Protrusions and recesses are considered advantageous as they may provide a positive indication to the user when they are in a locked position. For example when a user applies a force to the disconnecting member it will be evident if the features are locked together as the disconnecting member will not be moved when a smaller force is applied.

The protrusion may, for example, be located on the body member of the fluid transfer device or on an adapter fitted thereto. The recess may be located on the disconnecting member. However it will be appreciated that the arrangement of engagement features could be the other way around or indeed any combination thereof could be provided—e.g., with some protrusions on one part and other protrusions on the other part. It will be appreciated that there may be any number of engagement features depending on the application of the device. For example the device may be provided with more engagement features to increase the force necessary to move the connecting member.

In a set of embodiments the engagement features are designed such that there is a smooth transition from engagement to non-engagement. This may be achieved through chamfered or rounded edges on the engagement features. Such a smooth transition may be advantageous in some circumstances to prevent an excessive force being applied to the hub.

In a set of embodiments the engagement features are visible to the user. Such embodiments may be advantageous in ensuring the user is aware of the state of the lever member when connecting a hub to the fluid transfer device. The disconnecting member may be clear or translucent thus enabling the user to see through the surface of the disconnecting member to determine whether the engagement features are in engagement with one another. Alternatively the engagement features may extend through an external surface of the disconnecting member. For example a protrusion on the body member having a non-circular cross-section could extend through a corresponding aperture on the disconnecting member enabling it to be seen by the user.

In a set of embodiments in which the disconnecting member may include a lever member, the engagement parts are positioned behind a point at which the lever member pivots. This ensures that the force applied to the lever initially goes towards deforming the lever member and separating the engagement features instead of causing the lever member to become detached from its pivot points.

In accordance with the invention the hub may be retained on the tip purely by the friction fit. In a set of embodiments however the disconnecting member may include locking means for holding the hub. This may help the hub to be held onto the tip more securely.

In a set of embodiments the locking means is provided by a latch or other positive connection. For example, a suitable positive connection may be achieved by engaging a pair of male/female parts. This ensures that there is a strong positive connection with the hub and only allows removal of the hub when the lever is depressed. Some non-limiting examples of a latch may include a single protrusion, a series of protrusions or a saw-tooth profile.

In a further set of embodiments the locking means may include a screw thread provided on a lever member providing the disconnecting member. This provides a mechanism for locking a suitably configured hub, e.g., a standard Luer lock hub, onto the device. The hub may be connected by relative rotation between it and the body member, as is conventional, to ensure a tight screw connection. Such a Luer lock connection may be suited to high pressure fluid transfer procedures.

In such arrangements the lever member may be arranged such that movement of the front portion of the lever member relative to the body member causes the screw thread to pivot away and release the screw fit so that a hub can be disconnected from the device without an unscrewing action. The usual two-handed operation of unscrewing can thus be replaced by a simple one-handed operation of the lever member.

It is not essential that the hub also carries a screw thread. For example if the screw thread on the lever member does not extend all the way around the hub, the hub may be engaged though a simple annular flange, such as is found on a standard Luer slip hub, with the screw thread engaging the flange to provide a positive connection in addition to the friction fitting. Other hub designs may also be positively engaged by the screw thread, as is explained further below.

The Applicant has appreciated that locking the lever member in position, by means of the engagement features, is also beneficial when using threaded or flanged hubs with a threaded collar on the lever member. When screwing a screw threaded hub or hub with a flange onto a device without the lever member locked in position, there may be a tendency for the lever member to be pulled forward, due to the threaded hub pulling on the collar, in such a way that the collar might slip off the thread or flange. In this case when screwing the hub in further it would not be possible to obtain a desirably tight connection between the hub and male connector tip. With the engagement features of the present invention this problem may be overcome. The engagement features may prevent the lever member from moving in reaction to the pulling force referred to above. Consequently as the hub is screwed onto the collar the lever member is kept in an engaged position, with the threaded collar held close to the male connector tip, and a tight fit can be made with the male connector tip. Furthermore, when the disconnecting member is in the locked position, and the engagement features are in engagement with one another, a pulling force provided by the collar as the hub is screwed in to the collar, pulls the sidewalls of the disconnecting member inwards, and further tightens the engagement of the engagement features thus preventing the disconnecting member from moving.

The screw thread mounted on the lever member can be considered a kind of latch, as pivoting the lever member releases the latch so that the screw thread is separated from a corresponding thread on an outer surface of the connected hub. This leaves the hub connected by the friction fitting alone. Simply releasing the screw fit is not enough to disconnect the hub from the fluid transfer tip; the hub cannot fall away from the tip under gravity due to the friction fitting. The lever member of preferred embodiments of the invention has the additional function of also releasing the hub from the friction fitting. This may be achieved in a single smooth action by the lever member, for example a front surface of the front portion moving relative to the fluid transfer tip to push away the hub and release the friction fitting. In a preferred set of embodiments the lever member is pivotally connected to the body member of the device with one end, such as a front surface, moveable between first and second positions relative to the fluid transfer tip.

As is mentioned above, a hub may be connected to the fluid transfer device by pushing and rotating the hub, thus engaging the thread on the hub with the threaded collar. For example, a standard Luer lock hub may be rotated by up to 270° to ensure connection of its outer screw thread with the screw thread mounted on the lever member. During this process the lever member may remain locked in its engaged position while the hub is being connected. However, the Applicant has recognised that the time and/or manual dexterity required to rotate a hub to form the screw fit may not always be desirable. In accordance with embodiments of the invention however, an over-threshold force can be applied to the rear portion of the lever member to pivot the screw thread or other locking means provided on the front portion of the lever member away from the tip. A hub can then be pushed onto the male connector tip. A final, short rotation of the hub may then allow the screw thread to engage. This may provide an improvement over standard Luer lock connections as it may only require a turn through 90° (or less), rather than 180° or 270°, to complete the screw fit connection.

In a set of embodiments the screw thread on the lever member is only partial. For example the screw thread may be an internal thread carried by a partial or hemi-cylindrical collar. As such a collar only extends around one side of the fluid transfer tip, e.g., up to 180° around the circumference of the fluid transfer tip, the screw fit may be released simply by pivoting the lever member to move the collar away from the fluid transfer tip and hub connected thereto.

More generally, it is preferable that the screw thread provided on the lever member takes the form of an internally threaded collar. Such a collar may be provided on the lever member to at least partially surround the fluid transfer tip. In order to ensure a secure Luer lock connection, the internally threaded collar may extend substantially 360° around the circumference of the fluid transfer tip. However a 360° collar can make it more difficult for the lever member to operate to release the screw fit, as the collar must be moved away from the fluid transfer tip on all sides. The internally threaded collar may be separable into multiple segments that are arranged to be moved apart by pivoting the lever member to disengage the engagement features and thereby release the screw fit with the hub.

Such a fluid transfer connection benefits from the screw fit of a standard Luer lock connection, which is trusted to withstand pressurised fluid transfer procedures, the quality of the connection is ensured as the lever member is locked in position. The connection also enables the Luer lock connection to be released by operating the lever member instead of unscrewing the tip from a corresponding hub. This can be a simple one-handed gesture rather than a two-handed twisting movement. The separable collar allows the lever-operated disconnection mechanism to cooperate with a standard Luer lock hub.

In a set of embodiments the locking means is carried by a collar provided on the disconnecting member such that the hub can be mounted to the tip by initially applying a force to the disconnecting member to disengage the engagement features and move the collar away from the tip, and when the hub has been pushed onto the friction tip, the disconnecting member can be returned to a position whereby the locking means on the collar engages with the hub. Such an embodiment is advantageous as it allows the user to easily mount the hub on the device without having to overcome the locking means when attaching the hub. This is particularly advantageous when the locking means is provided by a latch which might require significant force to push the hub past the latch.

A potential problem with pushing a hub away from a tip is that it may be forcibly disconnected. If the hub is carrying a needle or other sharp object then this could pose an injury risk. In a set of embodiments therefore the device further may include a catch means arranged to catch the hub after it has been released from the friction fitting. Further movement of the disconnecting member (e.g., against a resilient bias) may cause the catch means to catch the hub. In this way the hub may be caught as it becomes disconnected but then controllably separated from the device. The catch means be may be subsequently released by resiliently biased movement of the disconnecting member, e.g., back to its resting state.

In a set of embodiments the disconnecting member is moveable between two positions: a first position wherein the front portion proximal to the male connector tip is close to the base of the tip and a second position wherein the front portion moves towards a distal end of the male connector tip. In a further set of embodiments the disconnecting member is resiliently biased such that it returns to its first position when no force is applied to the disconnecting member. This may be advantageous as it means that the device may always be in a state whereby a hub can be attached.

In a further set of embodiments the resilient bias is provided by the disconnecting member itself. This is advantageous as the lever member can be designed such that the deformation of the lever member, required to separate the engagement parts, acts to resiliently bias the disconnecting member back to its first, locked, positioned. In a set of embodiments the disconnecting member is made from an elastically deformable material. In a preferred set of embodiments the disconnecting member is made from plastic which can provide an inexpensive, sterile, and disposable product for single use in a medical setting.

Although the disconnecting member may take many different forms, preferably the disconnecting member may include a front surface that is substantially transverse to the axis of the tip and the front surface is arranged to move along the tip from a first position to a second position when force to disengage the engagement features is applied to the disconnecting member. In order for the disconnecting member to transfer force efficiently, it is preferable for it to be relatively stiff. The disconnecting member may be stiffened by forming it as a three-dimensional shell—i.e., with a shape that extends significantly in all three dimensions.

In a set of embodiments the disconnecting member may include a front surface that is substantially transverse to the axis of the tip and one or more side surfaces that extend in a direction substantially parallel to the axis of the tip. The surfaces may form a shroud extending at least partly around an axis defined by the tip—e.g., by at least 90 degrees. The shroud preferably extends back from the front surface, away from the fluid transfer tip. The three-dimensional extent of the member can help to ensure that it is stiff even if formed of a plastics material yet is still deformable to allow the engagement features to separate. In such embodiments, when a force is applied to the disconnecting member it causes the side surfaces of the disconnecting member to expand, thus disengaging the engagement features and allowing the disconnecting member to move relative to the body member.

In a further set of embodiments separate resilient means are provided between the disconnecting member and the body member. This may be in the form of a spring or any piece of elastically deformable material. This may be advantageous to ensure that the disconnecting member returns to its original, locked position to ensure the screw thread connection is secure, irrespective of any resilience of the disconnecting member itself.

The body member comprising at least one of the engagement features may be integral with or separate from the fluid transfer tip. In one set of embodiments the body member may include an integral mounting arrangement for the disconnecting member. In embodiments where the body member is integral with the fluid transfer tip, it may be positioned behind the fluid transfer tip, for example carried by a fluid chamber that is integrated with the tip.

In one set of embodiments the fluid transfer device may include a fluid chamber in communication with the fluid transfer tip and the body member is integrated with the fluid chamber. For example, the body member may include an axle integrated with the fluid chamber for pivotally mounting a disconnecting member in the form of a lever member. In a set of embodiments one of the engagement features is integrated with the fluid chamber. In such examples, the fluid transfer device may include a syringe and the syringe barrel may have an axle moulded on its outer surface to pivotally mount the lever member along with an engagement feature moulded on its outer surface to engage the corresponding feature on the lever member. The fluid chamber, such as the barrel of a syringe, may therefore be designed to mount a disconnecting member so that the device can be supplied with the disconnecting member pre-mounted ready for use.

In another set of embodiments the disconnecting member could even be integrated with the body member, for example as a lever member pivotally mounted by an integral hinge and held in a locked position by means of complementary engagement features on the body member and the lever member respectively. The lever member and body member could, for example, be formed as a single plastics moulding, e.g., with the lever member pivotally mounted by a living hinge or the like.

However, in another set of embodiments it may be desirable to retrofit a disconnecting member to an existing fluid transfer device or connection. For example, it may be desirable to mount a lever member to a standard syringe or other device/connection—via a suitable body member which may grip the syringe etc.—so as to enjoy various of the benefits outlined above but without changing the design of the device/connection. In such embodiments it is preferable that the disconnecting member is mounted by a separate body member. The body member may be attached to a fluid transfer device or connection by any suitable means. So as to avoid interference with the fluid transfer tip, the body member may be attached to the aft end of the tip, or behind the tip, e.g., by an attachment collar which grips the body. In a set of embodiments the body member may include means for gripping a barrel, hose, or other suitable portion of a fluid transfer device. The gripping means, could, for example, include one or more elastically compliant fingers made from a high friction material such as synthetic rubber.

When viewed from a second aspect the invention provides a connector for a fluid transfer device comprising a fluid transfer tip including a tapered friction fitting for a corresponding hub, the connector providing:
 a body member;
 a disconnecting member having a front portion and a rear portion; and
 engagement features operating between the disconnecting member and the body member which engage with one another to inhibit the front portion of the disconnecting member moving relative to the body member;
 the device being arranged such that upon application of a force to the rear portion of the disconnecting member, the disconnecting member deforms so that the engagement features are no longer in engagement with one another, thereby allowing the front portion of the disconnecting member to move relative to the fluid transfer tip and subsequently release the hub from the friction fitting.

It will be understood that such a retrofitting adapter may be attached around the fluid transfer tip or any other part of a fluid transfer connection or device, such as a syringe, in any situation where operation of the lever member may assist in locking and subsequently disconnecting a hub to/from the tip. The adapter may be attached before or after inserting the tip into a hub. Such an adapter could be optionally attached to a fluid transfer device or connection by a user when it is determined that the friction fitting is too tight to be easily disconnected by pulling the tip away from the hub, or at least not without risking damage or injury. The mechanism could also be optionally attached where the fluid transfer device (or connection) is connected to a hub carrying a needle and protection from needle spike is desired.

In one set of embodiments of either aspect of the invention the disconnecting member is removably mounted to the body member. This means that a user may remove and discard the disconnecting member if it is not required or if it is preferable to operate the device (or connection) without any interference from the disconnecting member.

The fluid transfer device may include any type of device used to transfer fluid—liquid and/or gas—either to or from a fluid receptacle. The fluid receptacle may be inanimate or it may be part of a living subject, for example a bodily cavity, organ, or vessel, such as a vein or artery. The present invention may find a wide range of uses, for example it could be employed for containers of dangerous or hazardous liquids—e.g., glue—where it is desirable to be able to detach a cap whilst avoiding contact with a user's hand. In a preferred set of embodiments however the fluid transfer device is a medical device. The fluid transfer device may include one or more devices such as a syringe, pre-filled syringe, IV delivery device e.g., "drip", transfusion device, fluid pump, stopcock, aspirator, suction device, container for a blood collection tube or hose. Alternatively the fluid transfer device could include a luer lock/luer slip male/female "bridge extension", which would enable the one-hand use functionality described herein to be added to an existing device. The device may be made to meet the relevant medical standard(s), for example ISO 7886 for sterile hypodermic syringes.

These and other features and improvements of the present application and the resultant patent will become apparent to one of ordinary skill in the art upon review of the following detailed description when taken in conjunction with the several drawings and the appended claims.

BRIEF DESCRIPTION OF THE DRAWINGS

Some embodiments of the present invention will now be described, by way of example only, and with reference to the accompanying drawings, in which:

FIG. 16 shows the hub attached to the fluid transfer device in the locked position;

FIG. 17 is a cross sectional view of a fluid transfer device in accordance with the invention with the lever member in the locked position;

FIG. 20 is a cross sectional view of the fluid transfer device when the lever member has been depressed and the side walls of the lever member have expanded;

FIG. 21 is an enlarged view of the side walls of the lever member and fluid transfer device when the lever member is in the un-locked position;

DETAILED DESCRIPTION

Figure 1:
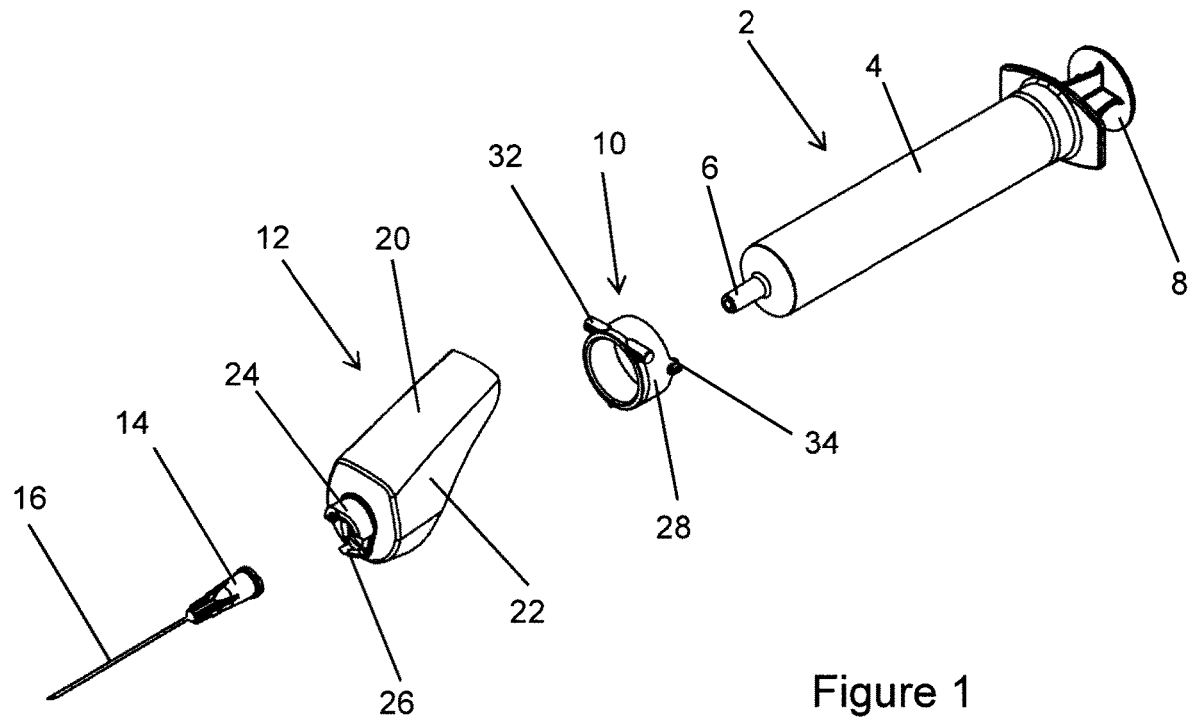
FIG. 1 is an exploded view of a fluid transfer device embodying the invention.

There may be seen in FIG. 1 an embodiment of a disconnecting mechanism for a fluid transfer device taking the form of a syringe 2. The syringe 2 generally may include a fluid barrel 4 in communication with a male tip 6. The tip 6 is tapered from its aft end, proximal to the barrel 4, to its forward end according to the standard Luer slip design i.e., a 6% taper (equivalent to around 3.43°). Fluid in the barrel 4 can be transferred through the tip 4 by pushing or pulling a plunger 8 inserted in the barrel 4. However, although a syringe 2 is shown in each of the embodiments for simplicity, such a Luer slip tip could equally be part of another fluid transfer device such as a drip, a hose connector or an "extension bridge" connector, as mentioned earlier.

FIG. 1 demonstrates how the syringe 2 can be connected with a body member in the form of an adapter 10, a lever member 12, and a female hub 14. In this embodiment the lever member 12 is attached to the adapter 10. This adapter can then be positioned on the syringe 2. The male connector tip 6 may be connected to a corresponding female hub 14 in order to transfer fluid to a needle 16 or other cannula mounted on the hub 14. Although not shown, the needle 16 might already be inserted into a living subject, for example for IV therapy with the hub 14 providing an IV port for the injection and/or removal of various fluids.

The tapered tip 6 is inserted into the hub 14 and forms a friction fit that is fluid-tight. In each of the embodiments, a lever member 12 is provided that can be manually operated to move relative to the male tip 6 between a first position, proximal to the syringe barrel and a second position spaced from the first position towards the distal end of the male tip 6 so as to push against the hub 14. Operation of the lever member 12 therefore acts to disconnect the syringe hub 14 from the tip 6 without a user needing to pull or tug the syringe hub 14 to release the friction fit of the Luer slip connection.

In the embodiment of FIG. 1 the lever member 12 is pivotally mounted to the adapter 10 which is attached to the syringe barrel 4. The adapter 10 can be held on the syringe 2 by any suitable means. This may be a friction fit or there may be locking features that hold the adapter on the syringe barrel 4. Alternatively the adapter 10 may include an internal thread and the syringe 2 may include an external thread to allow the adapter 10 to be screwed onto the syringe 2.

The lever member 12 may include a front surface 18 and rearwardly extending surface. The rearwardly extending surface may include a top surface 20 and side surfaces 22.

In the embodiment shown in FIG. 1 the lever member further may include a screw threaded collar 24 and a catch 26. The purpose of the threaded collar 24 is to engage with the hub 14 to lock it in position and the catch 26 is present to catch the hub 14 once it has been released from the male tip 6 by the lever member 12.

Figure 2:
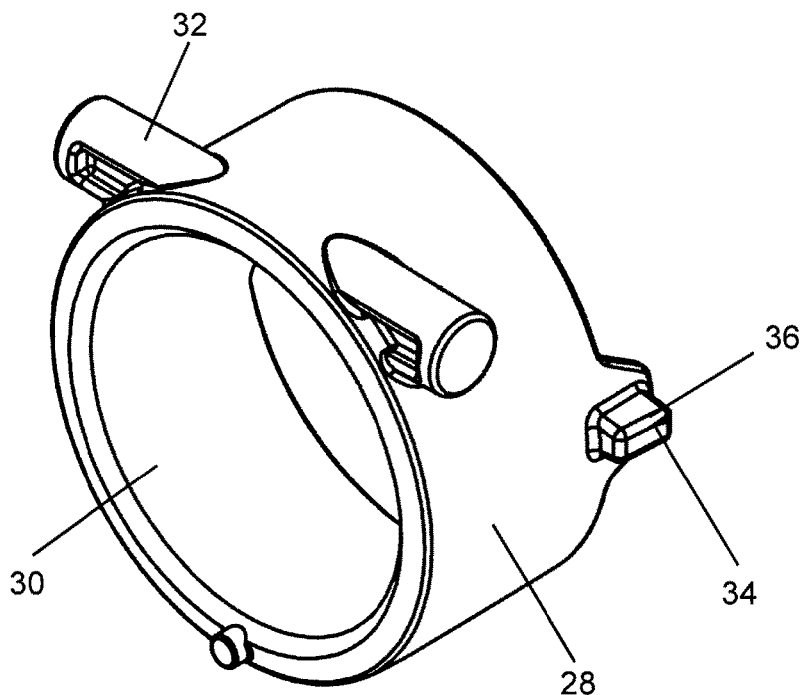
FIG. 2 is an enlarged view of the adapter of FIG. 1.

There is shown in FIG. 2 an enlarged view of the adapter 10. The adapter 10 has the general form of an annular band 28 enabling it to be fitted onto the syringe 2. The band 28 has a smooth inner surface 30. This inner surface 30 could be tapered or stepped to allow the adapter 10 to be fitted on to syringe barrels or other devices which have different diameters. In this embodiment the adapter is held on due to the frictional force between the adapter 10 and the outer surface of the syringe barrel 4.

The adapter may include two axle portions 32 integrally moulded at its forward end. These mount the lever member 12 to the adapter so that it can pivot about an axis defined by the axle portions 32. The adapter 10 further may include protrusions 34 extending from a rear part thereof. The protrusions 34 have chamfered edges 36 which ensure that they pass smoothly into and out of corresponding recesses on the lever member 12 as will be explained hereinbelow.

Figure 3:
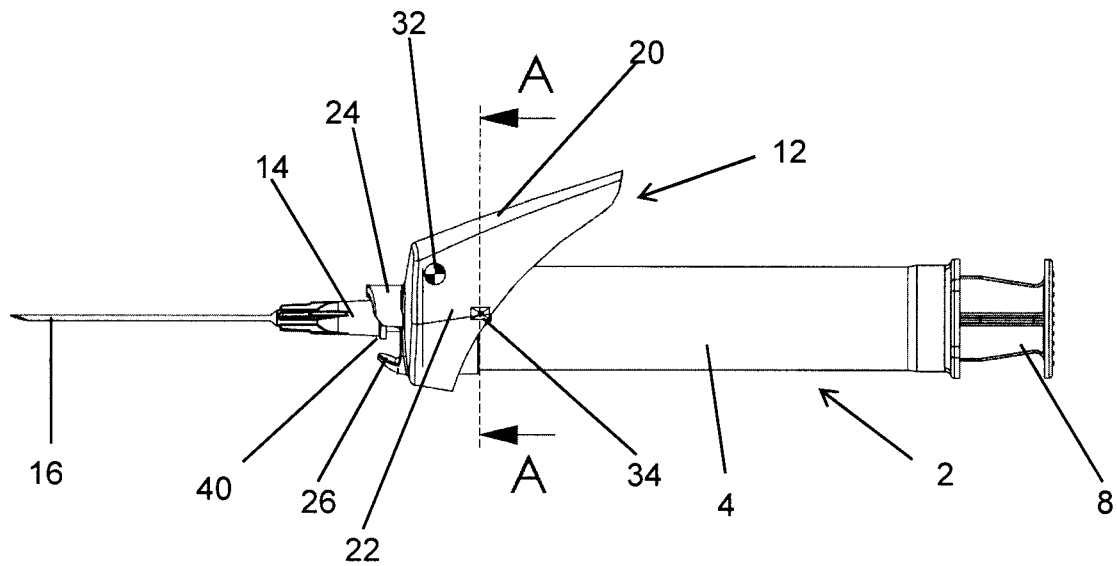
FIG. 3 shows the fluid transfer device in typical use.

FIG. 3 shows the fluid transfer device 2, adapter 10, lever member 12, and female hub 14 in normal use. The adapter 10 is positioned on the device 2 and the lever member 12 is pivotally mounted to the adapter 10 in such a way that pivotal movement is inhibited as is shown more clearly on the left hand side of FIG. 4. The female hub 14 can be screwed onto the male connector 6 tip by screwing it through the thread on the threaded collar 24. This is made possible as the hub 14 may include an annular flange 40. As the collar 24 is hemi-cylindrical in the embodiment shown, it is not necessary for the hub 14 to have a threaded section, an annular flange is sufficient to allow it to engage with the half screw thread 24. In different embodiments if the collar extends substantially around the male connector tip 6 then it may be necessary for the hub 14 to be threaded. The catch 26 on the lever member 12 prevents the hub 14 from being dangerously ejected from the device as will be explained later.

As seen in FIGS. 1 and 3, the lever member 12 is formed in a shroud shape which extends rearwardly and partially surrounds the adapter 10 and syringe barrel 4 through an angle of approximately 270°. Internal sockets (not shown) receive the axle portions 32 when the lever is clipped onto the adapter 10 to allow for pivotal movement between them. As shown in the left hand portion of FIG. 4 however, such pivotal movement is inhibited by the protrusions 34 on the adapter 10 being received in complementary recesses 38 on the inner surface of the side portions 22 of the lever 12. This can therefore be considered to be a locked position.

Figure 4:
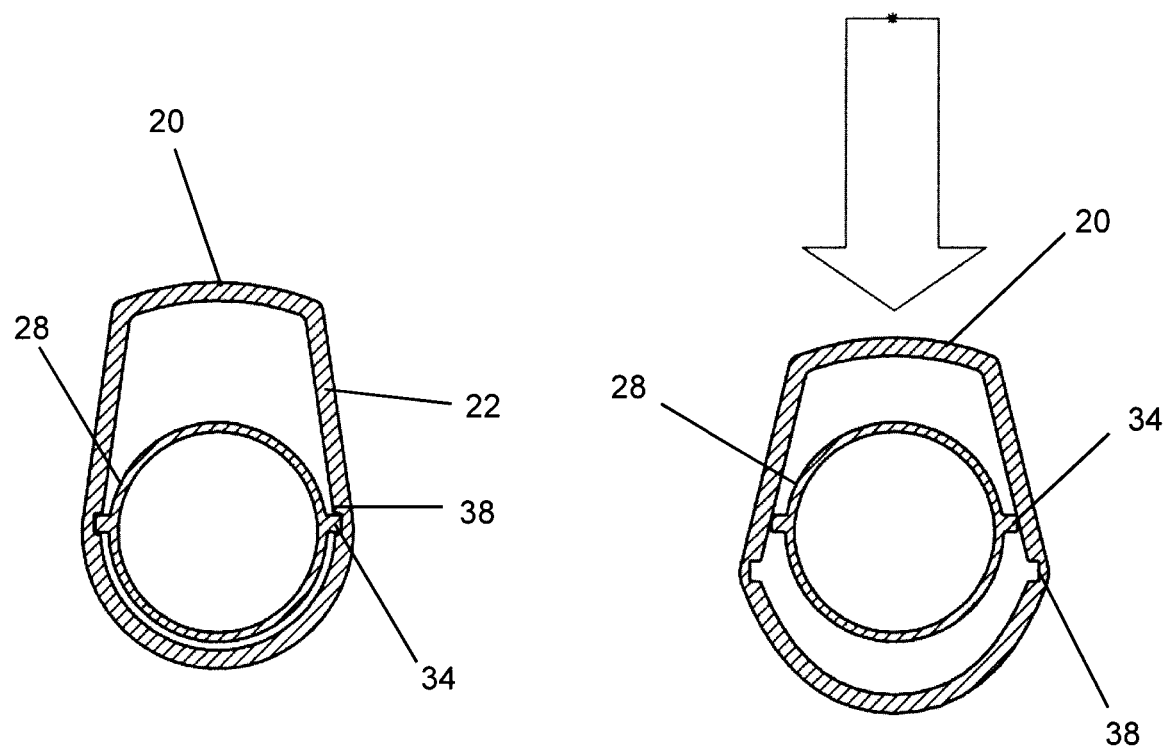
FIG. 4 is a pair of cross-sectional views on line A-A of FIG. 3 showing the lever member and corresponding adapter in both locked and unlocked positions.

The right hand side of FIG. 4 shows what happens when a user applies a force to the rear part 20 of the lever member. Pivotal movement is inhibited by the engagement between the protrusions 34 and recesses 38, but because the lever member 12 is moulded from a flexible plastic material the force applied to the rear part 20 of the lever causes the side surfaces 22 of the lever member to deform and bow out. As a result the recesses 38 are disengaged from the protrusions 34 and so the lever member 12 can then be pivoted about the axle portions 32.

In the embodiments shown the protrusions 34 and recesses 38 are positioned centrally about the axis of the fluid transfer device 2, however it will be appreciated that depending on the application they could be positioned away from the centre axis and further towards the top or the bottom of the adapter 10.

FIG. 4 illustrates that the shape of the lever member 12 can provide a resilient bias. Here the top portion 20 of the lever member is narrower in horizontal extent than the lower section. When the lower sections 22 are made to bow out by an applied force as in the right hand part of FIG. 4, when the force is subsequently removed, the deformed sides 22 tend to return to their original shape. As the top portion 20 is narrower than the lower portion 22, this pulls the lever member upwards 12 and thus causes the protrusions 34 and recesses 34 to become re-engaged, thus locking the lever member 12 in place once more.

Because the lever member 12 is locked into position unless pressure is applied to the rear portion 20, when the hub 14 is screwed into the threaded collar 24, the collar (which is an integral part of the lever member) resists the tendency to be drawn up by the hub 14 which would otherwise give rise to a tendency to slip off the flange 40 and so reduced the connection strength.

Figure 5:
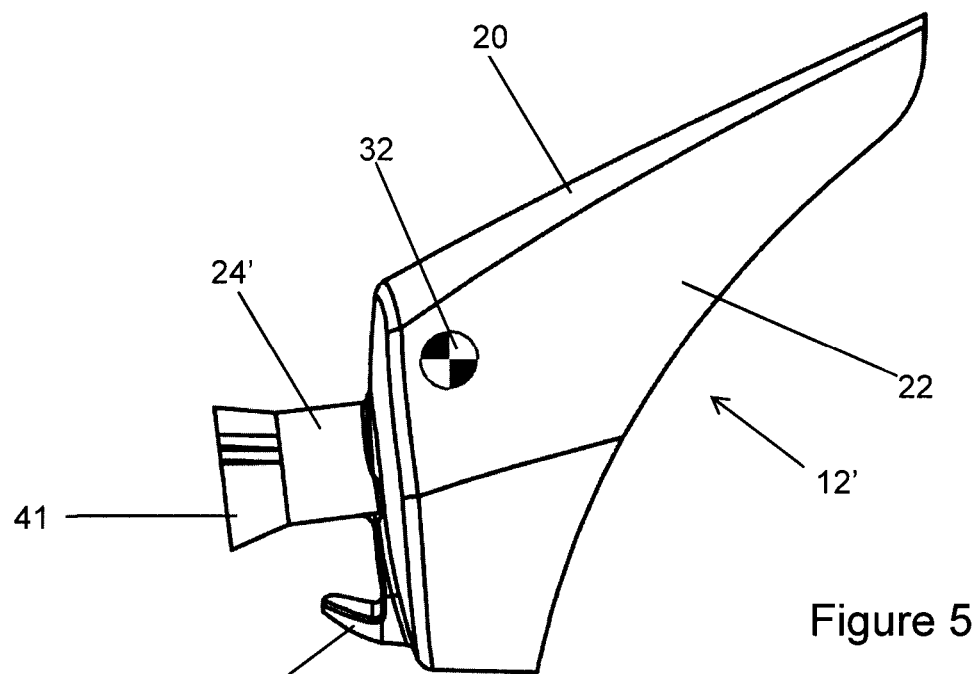
FIG. 5 is a close-up view of a lever member in accordance with another embodiment of the invention.
Figure 6:
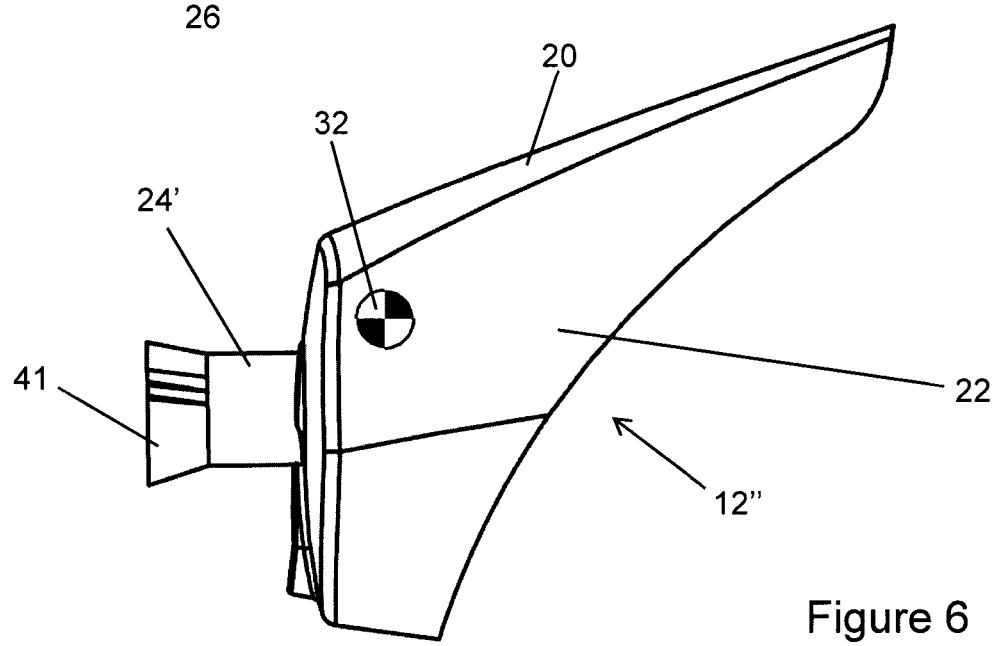
FIG. 6 shows a lever member similar to that of FIG. 5 without the catch.

FIG. 5 shows a different embodiment of the lever member 12'. The lever member 12' still has a shroud shape with a hemi-cylindrical collar 24' and a catch 26. However in this embodiment the collar 24' also may include split sections 41 which extend away from the collar 24' in a conical shape. This effectively increases the size of the opening of the collar 24' and makes it easier for the user to locate the female hub onto the device. FIG. 6 shows a similar embodiment except there is no catch provided.

Figure 7:
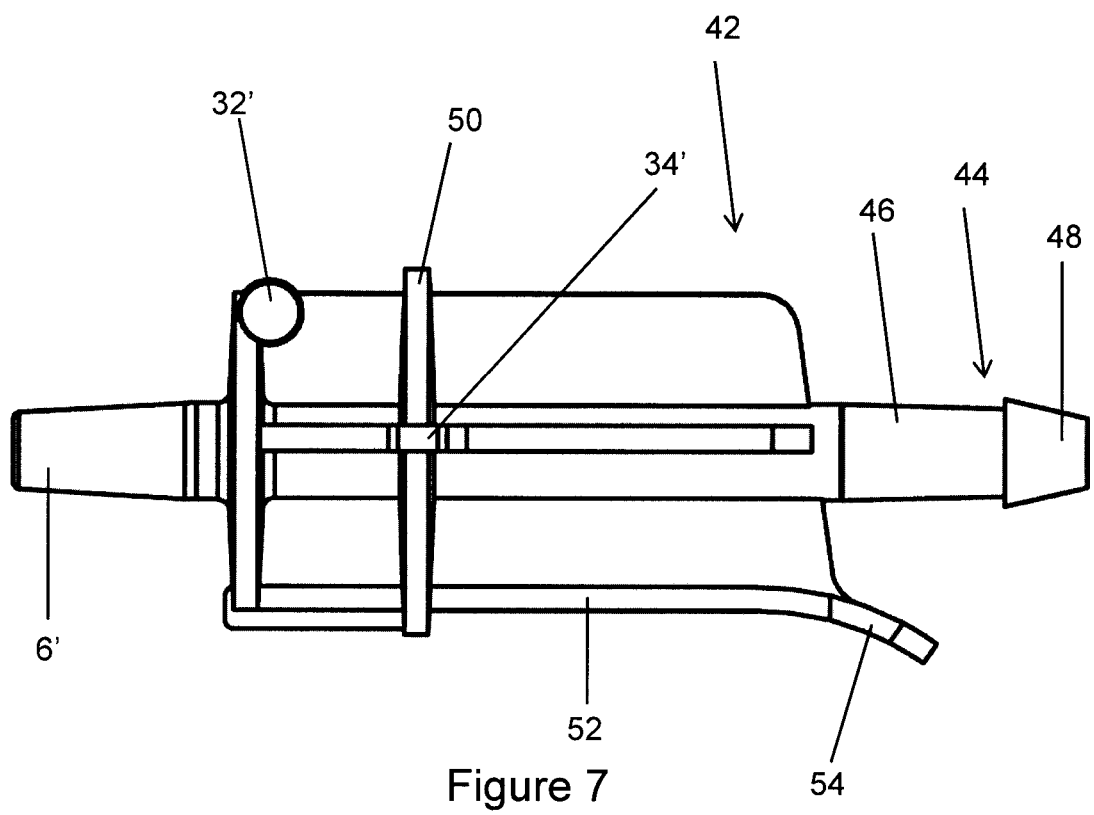
FIG. 7 shows another embodiment of a fluid transfer device wherein the axle and engagement features are integral.

FIG. 7 shows a further embodiment. In this embodiment instead of the annular adapter there is provided an adapter 42 that can be fitted directly to a hose or other fluid transfer device rather than a syringe. In this embodiment it can be seen that the aft end of the adapter 42 may include a nozzle 44 which can be connected to another device. This has a cylindrical section 46 with an enlarged frusto-conical end portion 48. This allows a hose or other device to be slid easily onto the end of the device and be held in place. In other embodiments (not shown) a similar adapter could be provided which forms a Luer lock/Luer slip male/female "bridge extension" which is able to connect to other devices which Luer lock/luer slip compatible—e.g., by including in the adapter a hub-like structure able to receive a standard male tip and a tip-like structure able to receive the hub bearing the needle.

The adapter 42 also may include an integral male connector tip 6' and the adapter 42 shown in FIG. 7 also may include axle portions 32' for enabling a lever member 12, 12' to be mounted to the adapter 42. Also seen on the side of the adapter 42 is one of two protrusions 34' which engage in complementary recess in the lever member to lock it into position as previously described. A reinforcing ring 50 of material ensures that when pressure is applied to the lever member it does not deform into the void space around the adapter and instead expands to disengage the protrusions 34'.

Also shown is a base plate 52 on the opposite side of the adapter 42 to the axle portions 32'. This has a curved rear portion 54. The base plate 52 is provided to allow the user to grip the adapter 42 securely. This assists both when positioning the female hub 14 on the male tip 6' and when releasing the hub 14.

Figure 8:
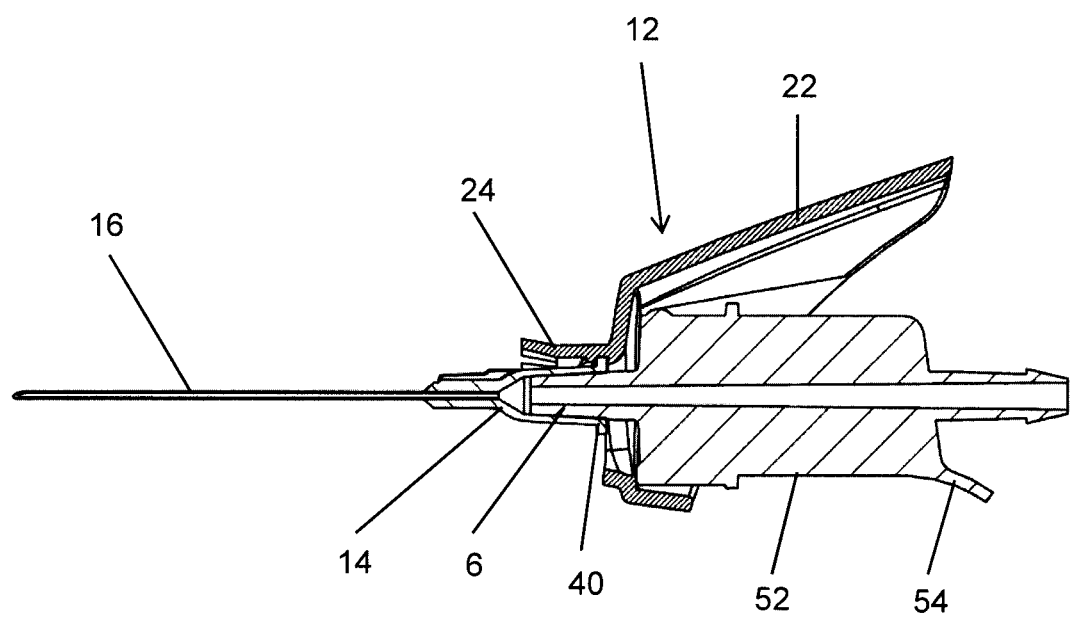
FIG. 8 is a sectional view of the fluid transfer device of FIG. 7 with a lever member and hub attached.

FIG. 8 shows an assembled implementation of the adapter 42 of FIG. 7, in which the female hub 14 has been placed on the male tip 6'. It can be seen that the flanged portion 40 of the hub is held in place by the internally threaded collar 24 on the lever member 12.

Figure 9:
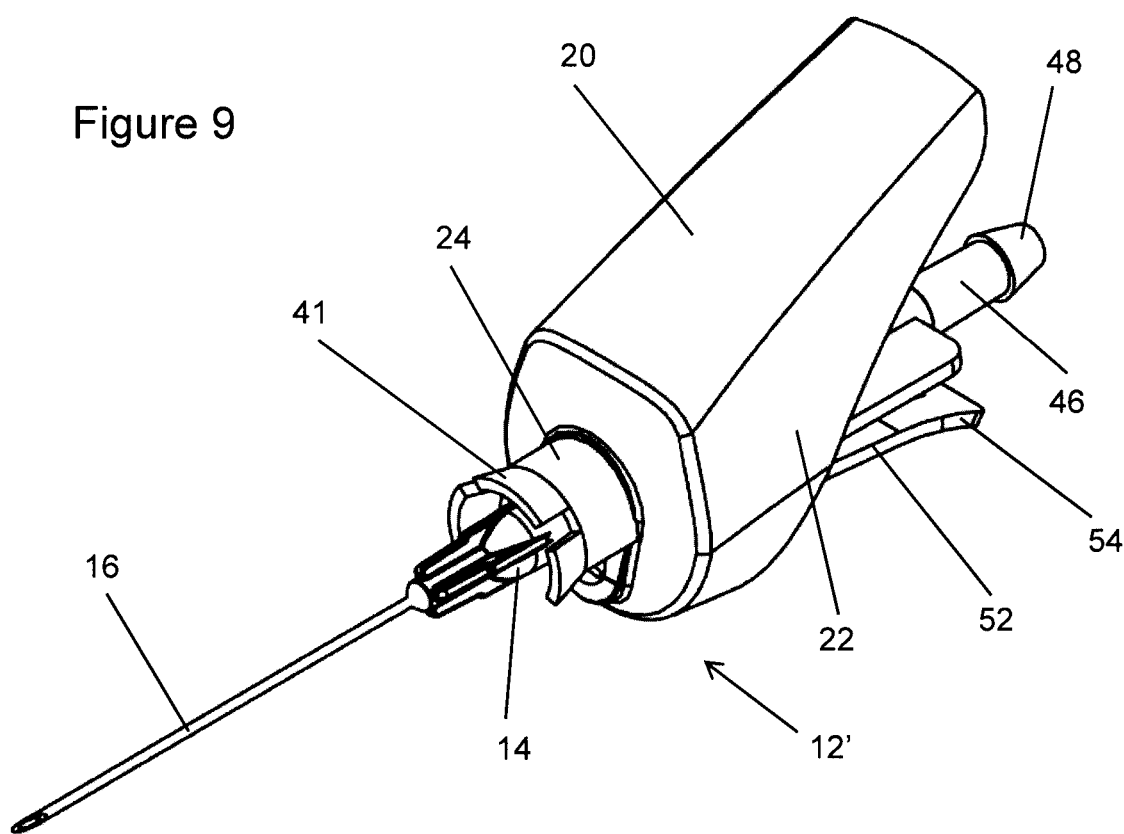
FIG. 9 is a perspective view of the fluid transfer device of FIG. 8.

FIG. 9 is another view of the same embodiment whereby the lever member 12' and hub 14 are shown. This figure shows where the user can grip both the lever member rear portion 20 and the base plate 52. In this figure the benefit provided by the split diverging portion 41 of the collar 24 can be seen since it effectively increases the aperture size of the collar, making guiding the hub 14 into the internally threaded collar 24 easier.

Figure 10:
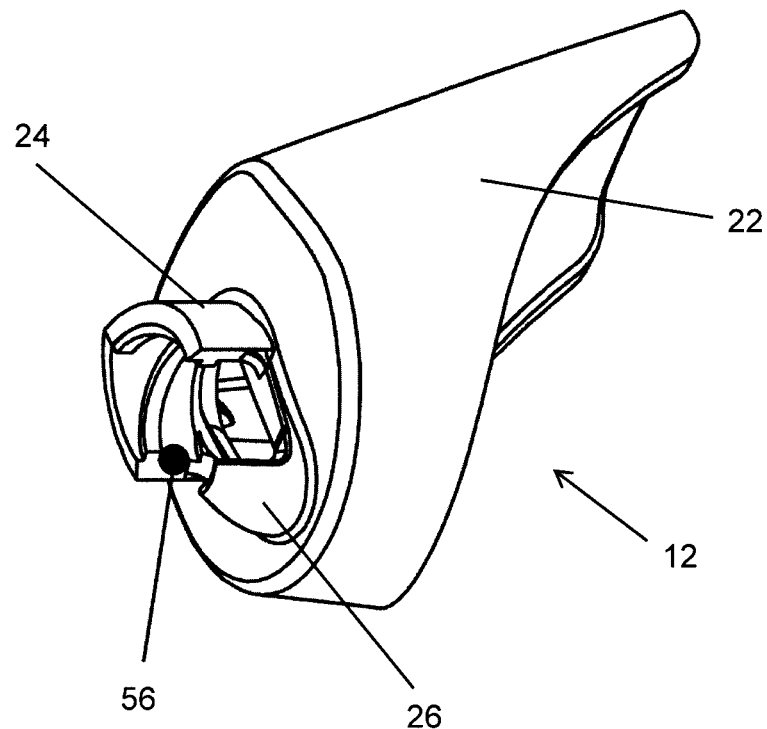
FIG. 10 shows another embodiment of the lever member with a threaded collar and catch integrally provided.

FIG. 10 shows the lever member 12 of FIG. 1. The threaded collar 24 may include half a turn of internal thread 56 which enables the user easily to screw the hub onto the device as it requires turning the hub (not shown) through a small angle to attach it.

Figure 11:
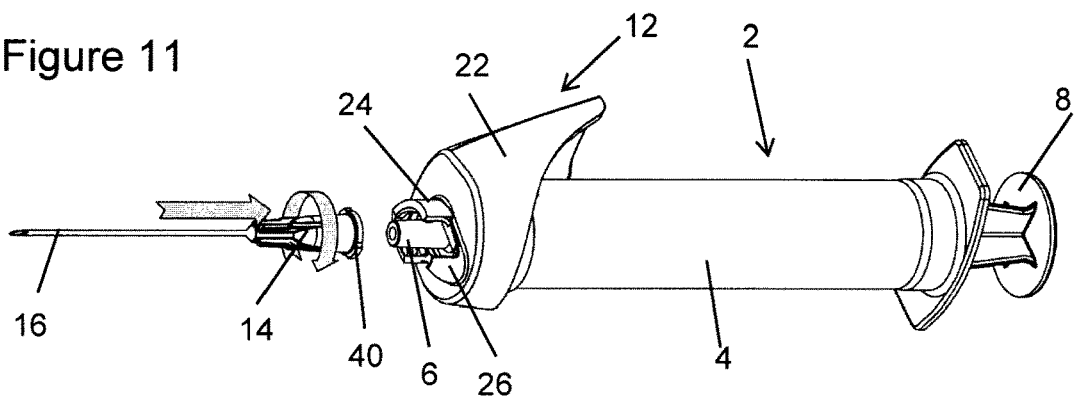
FIG. 11 shows the hub being screwed onto a fluid transfer device including the lever member of FIG. 10.
Figure 12:
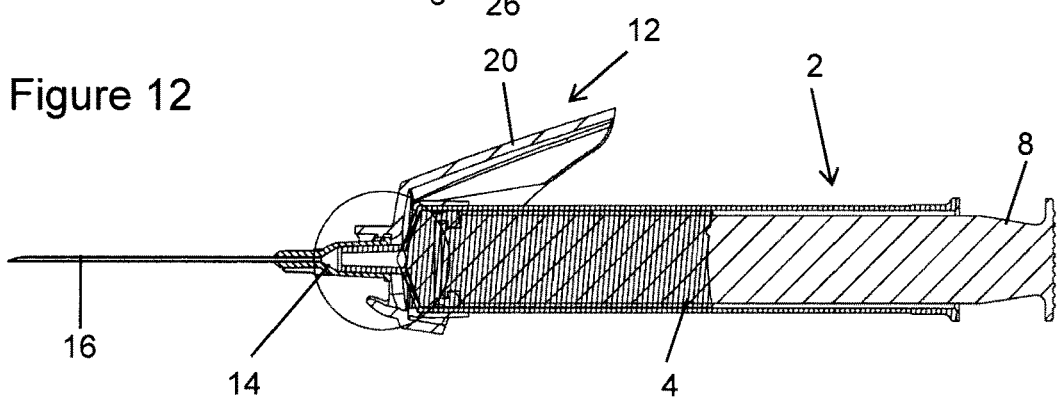
FIG. 12 is a sectional view of the embodiment of FIG. 11 with the hub in the locked position on the fluid transfer device.

FIGS. 11-14 show the sequence of events when a hub is attached to the device and later removed. As seen in FIG. 11 the device may include an adapter 10 carrying a lever member 12 attached to a syringe 2 as previously described, e.g., with reference to FIG. 1. The hub 14 bearing a needle 16 is attached to the syringe 2 by first by placing the hub 14 onto the male connector tip 6 and screwing it into position. During this the flange 40 on the hub engages with the internal thread on the collar 24. Throughout the attachment of the hub, the lever member 12 remains in the locked position whereby the protrusions 34 and recesses 38 are in engagement. This ensures that when the hub 14 is screwed on, the lever member 12 is not pulled towards the distal end of the male connector tip 6, thus ensuring a good connection between the hub 14 and male tip 6. Thus as the hub 14 is screwed on, the connection with the male tip 6 is improved and a better fluid-tight fit is achieved.

Once the hub 14 is fully screwed into position it is in a locked position. It is held in place by the friction fit provided by the male tip 6 and the threaded collar 24. This locked position can be seen in FIG. 12. In this state the user can apply pressure to the plunger 8 which will result in fluid being transferred through the male tip 6 and out of the needle 16.

Figure 13:
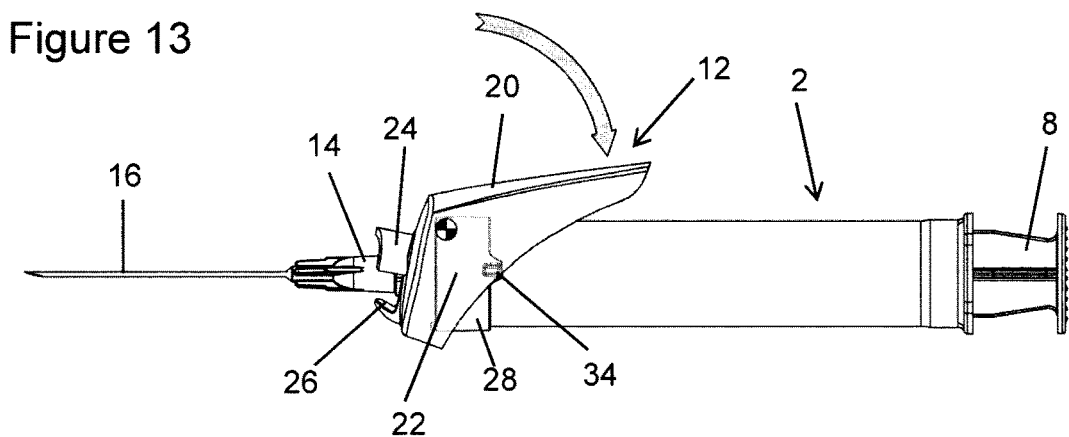
FIG. 13 shows the lever member being depressed in order to release the engagement features and release the hub.

When the user has finished using the device and wishes to remove the female hub 14, they simply apply pressure to the top surface 20 of the lever member 12. This process can be seen in FIG. 13. The applied pressure causes the side surfaces 22 of the lever member 12 to deform and thus the recesses 38 disengage from the protrusions 34. As soon as the recesses 38 are free from the protrusions 34, the force applied to the lever 12 causes it to rotate about the axle portions 32. This causes the threaded collar 24 to move away from the flange 40 on the hub 14 and the front surface of the lever member 12 to move towards a distal end of the male connector tip 6 pushing away the female hub 14. This acts to release the hub 14 from the friction fit. The catch 26 also moves towards the hub 14 to arrest its free movement and prevent it from being ejected dangerously from the device. At this stage, as shown in FIG. 13, the hub 14 is still loosely over the male tip 6, however it is held only by the catch 14.

Figure 14:
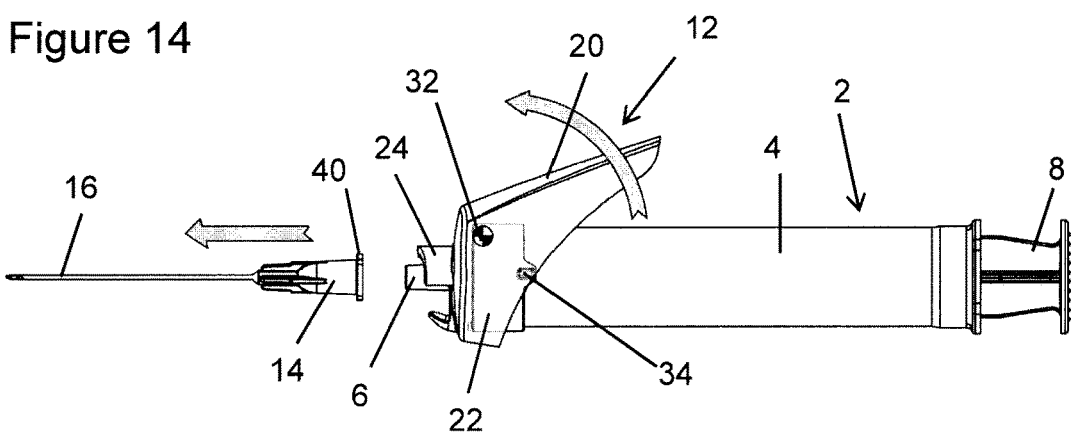
FIG. 14 shows the lever member being returned to its original position and the hub being released from the device.

When the user wishes to remove the female hub 14 completely for safe disposal, they can release the applied pressure to the lever member 12. This process is illustrated in FIG. 14. After the force being applied to the lever member 12 is released, the lever member 12 returns to its un-deformed state and so to its locked position as previously described with reference to FIG. 4. The hub 14 is thereby freed from the catch 26 and can be discarded appropriately in a sharps bin or other suitable place.

Figure 15:
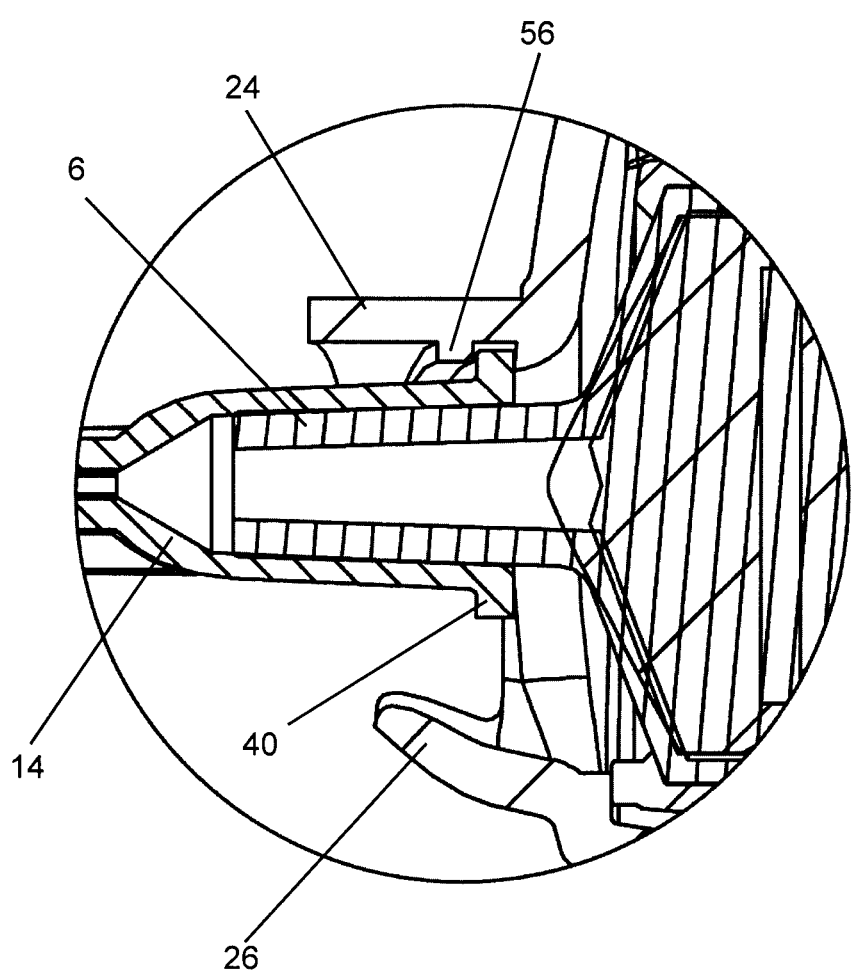
FIG. 15 is an enlarged sectional view of the hub being held in the locked position by the threaded collar.

FIG. 15 shows an enlarged view of the hub 14 when screwed onto the adapter and held in position by the threaded collar 24. The internal thread 56 grips the flange 40 on the hub 14. It is clear from this view that in this embodiment there is a minimal amount of thread 56 on the collar 24. This allows a quick and easy attachment of the hub 14 to the device since it is only necessary to turn it through a small angle. In situations where a stronger connection is required, for example where the pressures involved are higher, the collar 24 may be provided with more turns of thread 56.

FIG. 16 shows another view of all the components of FIG. 1 together in a locked position. It can be seen that the adapter 10 has been slid onto the chamber 4 of the syringe 2. FIG. 17 is a sectional view on line A-A of FIG. 16. It is possible to see how the axle portions 32 engage with sockets 60 on the lever member 12 providing a pivot axis. Also the protrusions 34 and recesses 38, which form the locking mechanism, can be seen.

Figure 18:
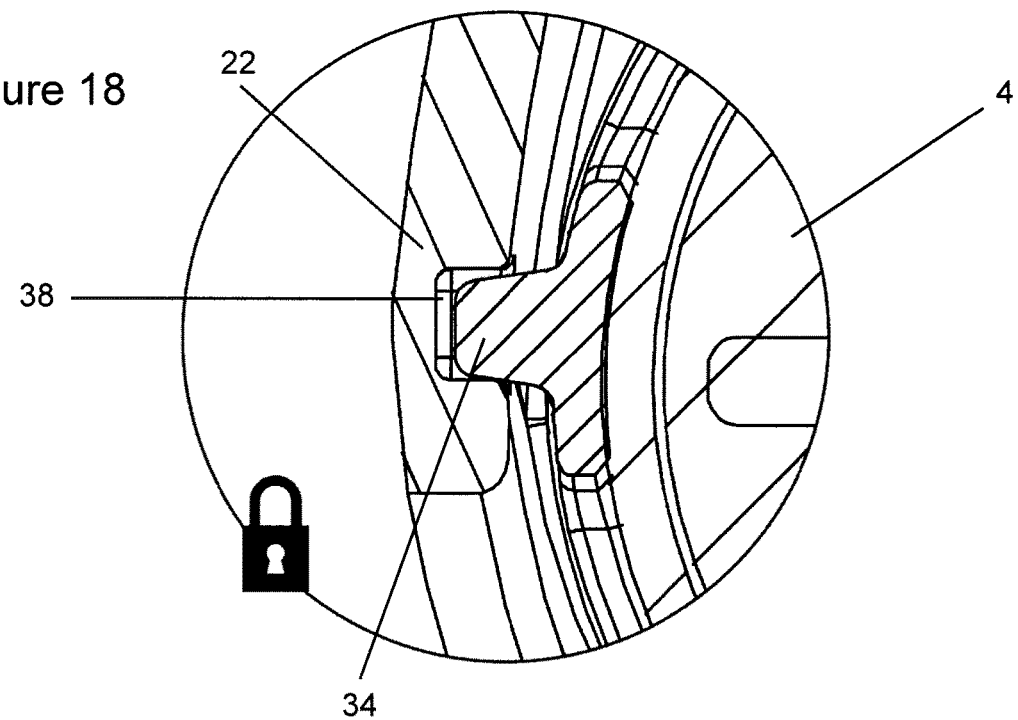
FIG. 18 is an enlarged view of the side walls of the lever member and body member of FIG. 17 when the lever member is in the locked position.

FIG. 18 is an enlarged view the circled area of FIG. 17 showing the protrusions 34 on the adapter 10 engaging with the recesses 38 on the side walls 22 of the lever member 12. It may be seen that the protrusion 34 is a relatively loose fit in the recess 38 to ensure that the protrusion 34 is reliably received in the recess 38 without becoming caught on the edge thereof. The small amount of play this permits is not sufficient to dislodge the hub 14. The Applicant has appreciated that several variations in the shape of the protrusion, and a tight/loose fit in the corresponding recess enable adjusting the design to an optimal function.

Figure 19:
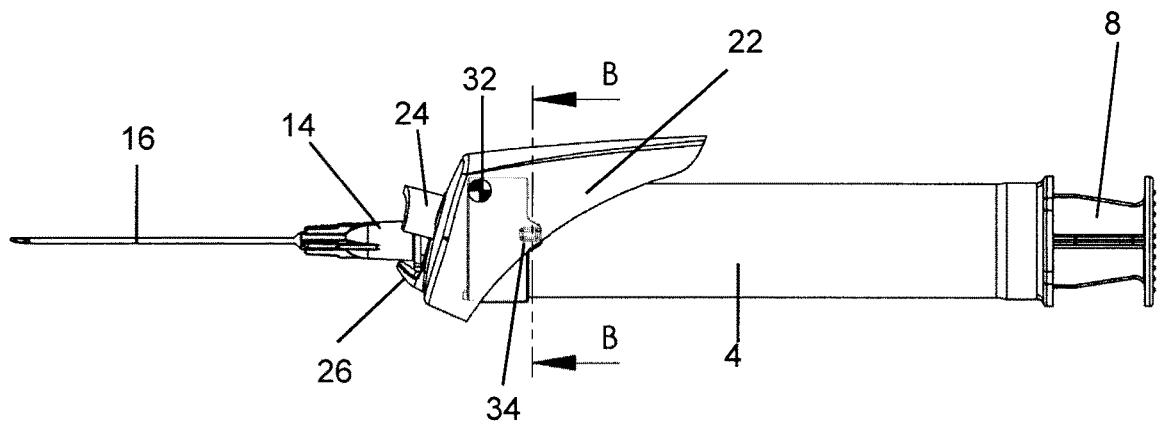
FIG. 19 is a view of the fluid transfer device when the lever member has been depressed.

FIGS. 19 to 21 correspond to FIGS. 16-18 for the case where the lever rear portion 20 is pressed down to release the lever 12. FIG. 19 shows the hub 14 disengaged and pushed away from its friction fit with the tip and so partially disconnected from the device as described above with reference to FIG. 13.

FIG. 20 shows how the side surfaces 22 of lever member 12 expand to disengage the engagement means. Applying a force to the top surface 20 of the lever member 12 it causes the protrusions 34 to press against the sides of the recesses 38. The force being applied therefore goes towards expanding the side surfaces 22 causing the lever member 12 to deform. This causes the sides 22 to bow out so that the recesses 38 separate away from the protrusions 34. Once the protrusions 34 and recesses 38 are out of engagement, the lever member 12 is free to rotate further.

Also visible in FIG. 20 are sockets 60 on the lever member 12 in the form of elongated slots. The slots 60 receive the axle portions 32 on the adapter 10. The slots 60 are elongated so as to accommodate the relative movement between the lever member 12 and the adapter 10 when the lever is depressed without the axles portions 32 becoming disengaged from the slots 60.

FIG. 21 shows an enlarged cross sectional view of the protrusions 34 and recesses 38 when the lever member 12 is in the unlocked position. It is clear that the sidewalls 22 of the lever member have expanded and the lever member 12 is free to pivot about the axle portions 32. As the lever member 12 pivots, the protrusions 34 move along the inside surface of the side walls 22. Although in the embodiment described the protrusions 34 pass along the inside surface, a groove may be provided on the inside surface of the sidewalls 22 to assist in directing the motion of the protrusion 34 and thus the lever member 12.

As described above, the hub 14 is typically attached to the device by pushing it onto the tip 6 whilst at the same time screwing it into the threaded collar 24. As an alternative method it is also possible first to depress the lever member rear portion 20, which disengages the protrusions 34 and recesses 38 and causes the lever member to pivot. The threaded collar 24 is pivoted away from the tip. The hub 14 can then be pushed onto the tip 6 and the lever member 12 can be released. The resilience of the lever member 12 causes it to return to its original locked position. The threaded collar 24 also returns to engage the flange 40 of the hub. The hub 14 can then be rotated a small amount to screw it into its final position. This method is advantageous as it requires minimal turning of the hub which may be difficult in instances where the hub is attached to a needle, or in instances where the hub is already attached to a living subject.

Figure 22:
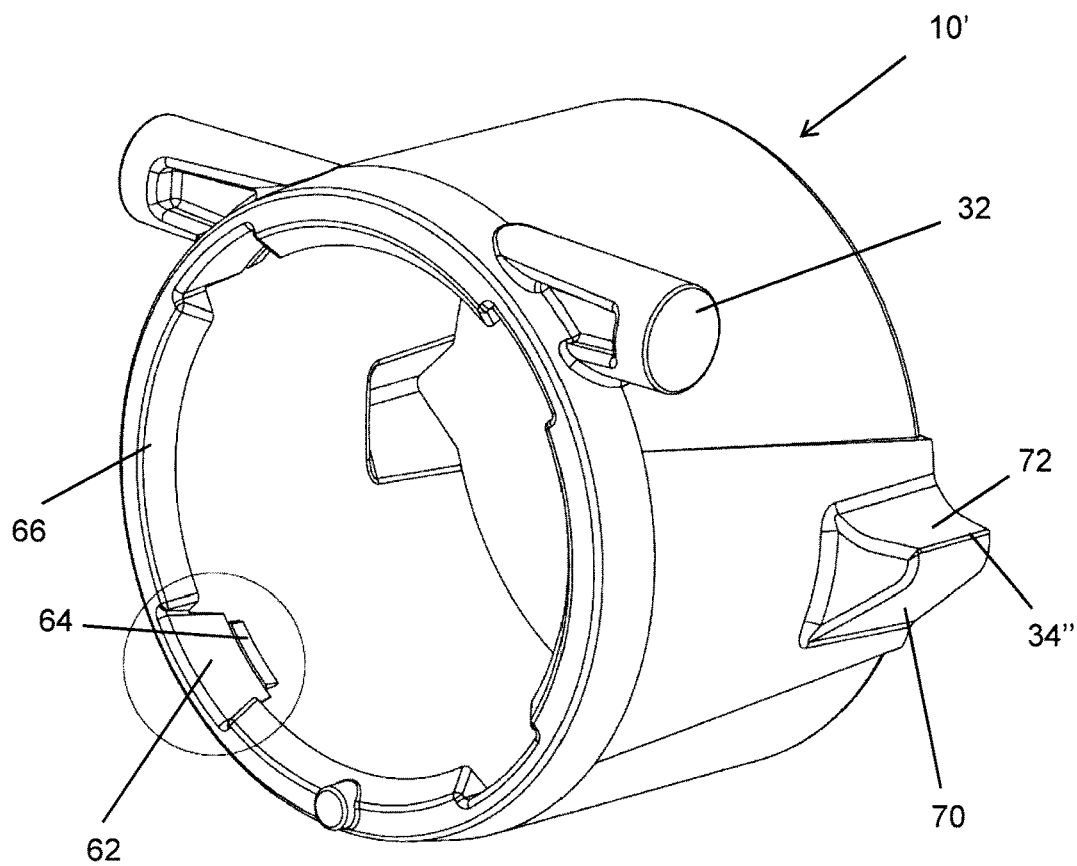
FIG. 22 is view similar to FIG. 2 of a further embodiment of an adapter in accordance with the invention.

FIG. 22 shows an alternative embodiment of an adapter 10'. This embodiment provides extra gripping means 62 on the adapter 10' to reduce the risk of the adapter being made to slip on the barrel 4 when a hub 14 is screwed onto the device. It can be seen that there are four high-friction gripping fingers 62 provided around the circumference of the adapter 10', however the number of and placement of these may vary depending on the application. The gripping fingers 62 are moulded as part of the adapter 10' and decrease its effective internal diameter to make a tighter fit. There also have clip sections 64 which may provide further grip or may lock into corresponding grooves on the barrel 4 of the device 2. The adapter 10' also may include a lipped section 66 which abuts against the front surface of the fluid transfer device 2 when it is fully on the device.

Also shown in FIG. 22 is an alternative form of protrusion 34". It can be seen that the protrusion 34" has a fin-like shape with a tapered edge 70 tapering towards the bottom of the adapter 10' and a horizontal edge 72. Such a protrusion 34" is advantageous as the horizontal edge 72 ensures that the lever cannot be pivoted downwards when the hub is being screwed on. It is only possible to dislodge the lever member 12 from the edge 72 when there is a significant force applied to the top surface 22 of the lever member 12. Furthermore the tapered face 70 ensures that when the pressure to the lever member 12 is removed, the recess on the lever member 12 can easily slide over the protrusion 34" and return to its locked position. This ensures that the device is always in a locked position when no force is being applied to the lever member 12.

Figure 23:
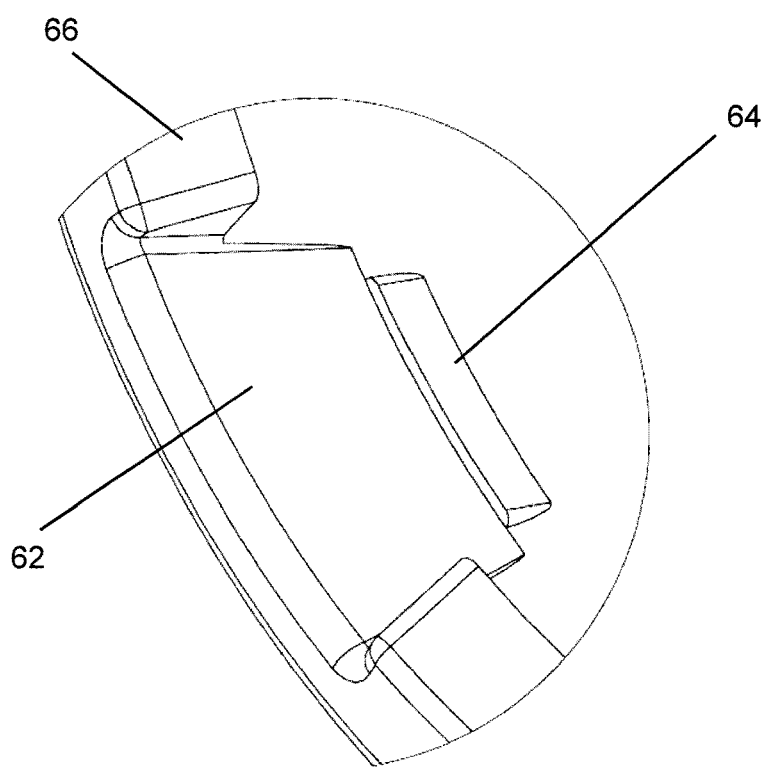
FIG. 23 is an enlarged view of the gripping features of FIG. 22.

FIG. 23 shows an enlarged view of the additional gripping fingers 62 provided on the adapter 10'. It is seen that the gripping fingers 62 are provided on the lipped section 66 at the end of the adapter. The adapter 10' is typically made from plastic, this allows the gripping means 62 to flex towards the wall of the adapter 10' during attachment to a device. This flexibility ensures that a strong grip is achieved with the fluid transfer device 2, and it also allows the adapter 10' to be used with devices that have slightly varying diameters In the embodiments shown the protrusions and axles are located on the adapter or fluid transfer device. However it is appreciated the both the axles and/or protrusions may be provided on the lever member and corresponding recesses may be provided on the adapter or fluid transfer device. Indeed there are many other possible ways in which engagement features could be provided to inhibit movement between the lever member and adapter.

It will be appreciated that it is not essential for an adapter to be provided—the invention could be implemented using a specially designed fluid transfer device. Moreover it is not essential to use a pivoting lever member—other forms of disconnecting member are contemplated such as a linearly sliding disconnecting member.

It should be apparent that the foregoing relates only to certain embodiments of the present application and the resultant patent. Numerous changes and modifications may be made herein by one of ordinary skill in the art without departing from the general spirit and scope of the invention as defined by the following claims and the equivalents thereof.

We claim:

1. A fluid transfer device for connection, in use, to a corresponding hub, the fluid transfer device comprising:
   a body member;
   a fluid transfer tip, the fluid transfer tip comprising a tapered friction fitting for the corresponding hub;
   a lever member pivotally mounted to the body member at a pivot point, the lever member having a front portion in front of the pivot point and a rear portion comprising one or more side surfaces extending behind the pivot point; and
   engagement features positioned behind the pivot point and operating between the rear portion of the lever member and the body member which engage with one another to inhibit the front portion of the disconnecting member from moving relative to the fluid transfer tip;
   the device being arranged such that, upon application of a force to the rear portion of the disconnecting member, the one or more side surfaces extending behind the pivot point deform so as to separate the engagement features such that the engagement features are no longer in engagement with one another, thereby allowing the front portion of the lever member in front of the pivot point to move relative to the fluid transfer tip and subsequently release the hub from the friction fitting.

2. A device according to claim 1, wherein the disconnecting member is a separate part from the body member.

3. A device according to claim 1, wherein the engagement features comprise at least one protrusion and at least one complementary recess.

4. A device according to claim 3, wherein the protrusion is located on the body member and the recess is located on the disconnecting member.

5. A device according to claim 1, wherein the engagement features are arranged such that there is a smooth transition from engagement to non-engagement.

6. A device according to claim 1, wherein the engagement features are visible to the user.

7. A device according to claim 1, wherein the disconnecting member comprises a locking arrangement for holding the hub.

8. A device according to claim 7, wherein the locking arrangement is provided by a latch or other positive connection.

9. A device according to claim 7, wherein the locking arrangement comprises a screw thread provided on a lever member providing the disconnecting member.

10. A device according to claim 9, wherein the lever member is arranged such that movement of a front portion of the lever member relative to the body member causes the screw thread to pivot away and release the screw fit.

11. A device according to claim 9, wherein the screw thread on the lever member is only partial.

12. A device according to claim 9, wherein the screw thread is an internal thread carried by a partial or hemi-cylindrical collar.

13. A device according to claim 9, wherein the screw thread provided on the lever member takes the form of an internally threaded collar.

14. A device according to claim 8, wherein the locking arrangement is carried by a collar provided on the disconnecting member such that the hub can be mounted to the tip by initially applying a force to the disconnecting member to disengage the engagement features and move the collar away from the tip, and when the hub has been pushed onto the friction tip, the disconnecting member can be returned to a position whereby the locking arrangement on the collar engages with the hub.

15. A device according to claim 13, wherein the internally threaded collar may be separable into multiple segments that are arranged to be moved apart by pivoting the lever member to disengage the engagement features and thereby release the screw fit with the hub.

16. A device according to claim 1, wherein the disconnecting member comprises a front surface that is substantially transverse to the axis of the tip and the front surface is arranged to move along the tip from a first position to a second position when force to disengage the engagement features is applied to the disconnecting member.

17. A device according to claim 1, wherein the disconnecting member is pivotally connected to the body member.

18. A device according to claim 1, wherein the device further comprises a catch arrangement arranged to catch the hub after it has been released from the friction fitting.

19. A device according to claim 18, wherein the catch arrangement is subsequently released by a resiliently biased movement of the disconnecting member.

20. A device according to claim 16, wherein the disconnecting member is resiliently biased such that it returns to its first position when no force is applied to the disconnecting member.

21. A device according to claim 20, wherein the resilient bias is provided by the disconnecting member itself.

22. A device according to claim 1, wherein the disconnecting member is made from an elastically deformable material.

23. A device according to claim 1, wherein the disconnecting member is relatively stiff.

24. A device according to claim 23, wherein the disconnecting member comprises a three-dimensional shell with a shape that extends significantly in all three dimensions.

25. A device according to claim 1, wherein the disconnecting member comprises a front surface that is substantially transverse to the axis of the tip and one or more side surfaces that extend in a direction substantially parallel to the axis of the tip.

26. A device according to claim 25, wherein the surfaces form a shroud extending at least partly around an axis defined by the tip.

27. A device according to claim 26, wherein the shroud extends back from the front surface, away from the fluid transfer tip.

28. A device according to claim 1, wherein the body member comprises an integral mounting arrangement for the disconnecting member.

29. A device according to claim 1, wherein the fluid transfer device comprises a fluid chamber in communication with the fluid transfer tip and the body member is integrated with the fluid chamber.

30. A device according to claim 29, wherein the body member comprises an axle integrated with the fluid chamber for pivotally mounting the disconnecting member in the form of a lever member.

31. A device according to claim 29, wherein one of the engagement features is integrated with the fluid chamber.

32. A device according to claim 29, wherein the fluid transfer device comprises a syringe including a syringe barrel and the syringe barrel has an axle moulded on its outer surface to pivotally mount the disconnecting member in the form of a lever member, and wherein the syringe barrel has one of the engagement features moulded on its outer surface to engage another one the engagement features arranged on the lever member.

33. A device according to claim 1, wherein it is possible to retrofit the disconnecting member to an existing fluid transfer device or connection.

34. A device according to claim 1, wherein the disconnecting member is mounted to the body member and the body member is attached to the device as a separate part.

35. A device according to claim 34, wherein the body member comprises an arrangement for gripping a barrel, hose or other suitable portion of the fluid transfer device.

36. A device according to claim 35, wherein the gripping arrangement comprises one or more elastically compliant fingers.

37. A device according to claim 1, wherein the disconnecting member is removably mounted to the body member.

38. A device according to claim 1, wherein the disconnecting member is formed integrally with the body member.

39. A fluid transfer device for connection, in use, to a corresponding hub, the fluid transfer device comprising:
a body member;
a fluid transfer tip, the fluid transfer tip comprising a tapered friction fitting for the corresponding hub;
a disconnecting member having a front portion and a rear portion comprising one or more side surfaces; and
engagement features operating between the one or more side surfaces and the body member which engage with one another to inhibit the front portion of the disconnecting member from moving relative to the fluid transfer tip;
the device being arranged such that upon application of a force to the rear portion of the disconnecting member, the one or more side surfaces of the rear portion of the disconnecting member deform and thereby expand so that the engagement features are no longer in engagement with one another, thereby allowing the front portion of the disconnecting member to move relative to the fluid transfer tip and subsequently release the hub from the friction fitting.

40. A fluid transfer device for connection, in use, to a corresponding hub, the fluid transfer device comprising:
a body member;
a fluid transfer tip, the fluid transfer tip comprising a tapered friction fitting for the corresponding hub;
a disconnecting member having a front portion and a rear portion comprising one or more side surfaces; and
engagement features operating between the one or more side surfaces and the body member which engage with one another to inhibit the front portion of the disconnecting member from moving relative to the fluid transfer tip;
the device being arranged such that upon application of a force to the rear portion of the disconnecting member, the one or more side surfaces of the rear portion of the disconnecting member deform and bow out so that the engagement features are no longer in engagement with one another, thereby allowing the front portion of the disconnecting member to move relative to the fluid transfer tip and subsequently release the hub from the friction fitting.

* * * * *